US011974811B2

(12) United States Patent
Jia et al.

(10) Patent No.: US 11,974,811 B2
(45) Date of Patent: May 7, 2024

(54) DETECTING AVASCULAR AND SIGNAL REDUCTION AREAS IN RETINAS USING NEURAL NETWORKS

(71) Applicant: OREGON HEALTH & SCIENCE UNIVERSITY, Portland, OR (US)

(72) Inventors: Yali Jia, Portland, OR (US); Yukun Guo, Portland, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 388 days.

(21) Appl. No.: 17/606,719

(22) PCT Filed: Apr. 24, 2020

(86) PCT No.: PCT/US2020/029941
§ 371 (c)(1),
(2) Date: Oct. 26, 2021

(87) PCT Pub. No.: WO2020/219968
PCT Pub. Date: Oct. 29, 2020

(65) Prior Publication Data
US 2022/0151490 A1 May 19, 2022

Related U.S. Application Data

(60) Provisional application No. 62/839,349, filed on Apr. 26, 2019.

(51) Int. Cl.
*A61B 3/12* (2006.01)
*A61B 3/00* (2006.01)
(Continued)

(52) U.S. Cl.
CPC .......... *A61B 3/1241* (2013.01); *A61B 3/0058* (2013.01); *A61B 3/102* (2013.01);
(Continued)

(58) Field of Classification Search
CPC ..... A61B 3/1241; A61B 3/0058; A61B 3/102; A61B 5/7267; G06T 7/0012;
(Continued)

(56) References Cited

U.S. PATENT DOCUMENTS

2017/0039689 A1 2/2017 Solanki et al.
2018/0132725 A1 5/2018 Vogl et al.
(Continued)

OTHER PUBLICATIONS

Wang, Jie, et al. "Reflectance-based projection-resolved optical coherence tomography angiography." Biomedical Optics Express 8.3 (2017): 1536-1548. (Year: 2017).*
(Continued)

*Primary Examiner* — Emily C Terrell
*Assistant Examiner* — Stefano Anthony Dardano
(74) *Attorney, Agent, or Firm* — Lee & Hayes P.C.

(57) ABSTRACT

This disclosure describes systems, devices, and techniques for training neural networks to identify avascular and signal reduction areas of Optical Coherence Tomography Angiography (OCTA) images and for using trained neural networks. By identifying signal reduction areas in OCTA images, the avascular areas can be detected with high accuracy, even when the OCTA images include artifacts and other types of noise. Accordingly, various implementations described herein can accurately identify avascular areas from real-world clinical OCTA images. In various implementations, a method can include identifying images of retinas. The images may include thickness images, reflectance intensity maps, and OCTA images of the retinas. Avascular maps corresponding to the OCTA images can be identified. A neural network can be trained based on the images and the avascular maps.

20 Claims, 13 Drawing Sheets

(51) Int. Cl.
    *A61B 3/10*     (2006.01)
    *A61B 5/00*     (2006.01)
    *G06T 7/00*     (2017.01)
    *G16H 30/40*    (2018.01)
    *G16H 50/20*    (2018.01)

(52) U.S. Cl.
    CPC .......... *A61B 5/7267* (2013.01); *G06T 7/0012* (2013.01); *G16H 30/40* (2018.01); *G16H 50/20* (2018.01); *G06T 2207/10101* (2013.01); *G06T 2207/20081* (2013.01); *G06T 2207/20084* (2013.01); *G06T 2207/30041* (2013.01)

(58) Field of Classification Search
    CPC . G06T 2207/10101; G06T 2207/20081; G06T 2207/20084; G06T 2207/30041; G16H 30/40; G16H 50/20; G06N 3/045; G06N 3/08
    See application file for complete search history.

(56) References Cited

U.S. PATENT DOCUMENTS

2020/0342595 A1    10/2020  Jia et al.
2022/0207729 A1*    6/2022  Boyd ................... G06V 40/193

OTHER PUBLICATIONS

Agemy, et al., "Retinal Vascular Perfusion Density Mapping Using Optical Coherence Tomography Angiography in Normals and Diabetic Retinopathy Patients," Retina, vol. 35, No. 11, Nov. 2015, pp. 2353-2363.
Alibhai, et al., "Quantification of Retinal Capillary Nonperfusion in Diabetics Using Wide-Field Optical Coherence Tomography Angiography," Retina, vol. 40, No. 3, Mar. 2020, pp. 412-420.
Antonetti, et al., "Diabetic Retinopathy," The New England Journal of Medicine, vol. 336, No. 13, Mar. 2012, pp. 1227-1239.
Badrinarayanan, et al., "SegNet: A Deep Convolutional Encoder-Decoder Architecture for Image Segmentation," IEEE Transactions on Pattern Analysis and Machine Intelligence, vol. 39, No. 12, Dec. 2017, pp. 2481-2495.
Camino, et al., "Deep learning for the segmentation of preserved photoreceptors on en face optical coherence tomography in two inherited retinal diseases," Biomedical Optics Express, vol. 9, No. 7, Jul. 2018, pp. 3092-3105.
Camino, et al., "Evaluation of artifact reduction in optical coherence tomography angiography with real-time tracking and motion correction technology," Biomedical Optics Express, vol. 7, No. 10, Oct. 2016, pp. 3905-3915.
Camino, et al., "Regression-based algorithm for bulk motion subtraction in optical coherence tomography angiography," Biomedical Optics Express, vol. 8, No. 6, Jun. 2017, pp. 3053-3066.
Chen, et al., "DeepLab: Semantic Image Segmentation with Deep Convolutional Nets, Atrous Convolution, and Fully Connected CRFs," IEEE Transactions on Pattern Analysis and Machine Intelligence, vol. 40, No. 4, Apr. 2018, pp. 834-848.
Chen, et al., "Rethinking Atrous Convolution for Semantic Image Segmentation," ArXiv, Dec. 2017, 14 pages.
Devalla, et al., "DRUNET: a dilated-residual U-Net deep learning network to segment optic nerve head tissues in optical coherence tomography images," Biomedical Optics Express, vol. 9, No. 7, Jul. 2018, pp. 3244-3265.
Fang, et al., "Automatic segmentation of nine retinal layer boundaries in OCT images of non-exudative AMD patients using deep learning and graph search," Biomedical Optics Express, vol. 8, No. 5, May 2017, pp. 2732-2744.
Gao, et al., "Compensation for Reflectance Variation in Vessel Density Quantification by Optical Coherence Tomography Angiography," Investigative Ophthalmology & Visual Science, vol. 57, No. 10, Aug. 2016, pp. 4485-4492.
Guo, et al., "Development and Validation of a Deep Learning Algorithm for Distinguishing the Nonperfusion Area from Signal Reduction Artifacts on OCT Angiography", Biomedical Optics Express, vol. 10, No. 7, Jul. 1, 2019, pp. 3257-3268.
Guo, et al., "Automated segmentation of retinal layer boundaries and capillary plexuses in wide-field optical coherence tomographic angiography," Biomedical Optics Express, vol. 9, No. 9, Sep. 2018, pp. 4429-4442.
Hamwood, et al., "Effect of patch size and network architecture on a convolutional neural network approach for automatic segmentation of OCT retinal layers," Biomedical Optics Express, vol. 9, No. 7, Jul. 2018, pp. 3049-3066.
He, et al., "Deep Residual Learning for Image Recognition," Computer Vision and Pattern Recognition, Jun. 2016, pp. 770-778.
Huang, et al., "Densely Connected Convolutional Networks," Proceedings of the IEEE Conference on Computer Vision and Pattern Recognition, Jul. 2017, pp. 4700-4708.
Hussain, et al., "Diametric measurement of foveal avascular zone in healthy young adults using optical coherence tomography angiography," International Journal of Retina and Vitreous, vol. 2, No. 27, Dec. 2016, 5 pages.
Hwang, et al., "Automated Quantification of Nonperfusion Areas in 3 Vascular Plexuses With Optical Coherence Tomography Angiography in Eyes of Patients With Diabetes," JAMA Ophthalmology, vol. 136, No. 8, Jun. 2018, pp. 929-936.
Hwang, et al., "Optical Coherence Tomography Angiography Features of Diabetic Retinopathy," Retina, vol. 35, No. 11, Nov. 2015, 14 pages.
Hwang, et al., "Visualization of 3 Distinct Retinal Plexuses by Projection-Resolved Optical Coherence Tomography Angiography in Diabetic Retinopathy," JAMA Ophthalmology, vol. 134, No. 12, Nov. 2016, pp. 1411-1419.
Jia, et al., "Quantitative optical coherence tomography angiography of vascular abnormalities in the living human eye," PNAS USA, vol. 112, No. 18, Apr. 2015, pp. E2395-E2402.
Jia, et al., "Split-spectrum amplitude-decorrelation angiography with optical coherence tomography," Optics Express, vol. 20, No. 4, Feb. 2012, pp. 4710-4725.
Joussen, et al., "A central role for inflammation in the pathogenesis of diabetic retinopathy," FASEB Journal, vol. 18, No. 12, Jul. 2004, 17 pages.
Karri, et al., "Transfer learning based classification of optical coherence tomography images with diabetic macular edema and dry age-related macular degeneration," Biomedical Optics Express, vol. 8, No. 2, Feb. 2017, pp. 579-592.
Kermany, et al., "Identifying Medical Diagnoses and Treatable Diseases by Image-Based Deep Learning," Cell, vol. 172, No. 5, Feb. 2018, pp. 1122-1131 (19 pages).
Kingma, et al., "Adam: A Method for Stochastic Optimization," arXiv, Jan. 2017, 15 pages.
Lee, et al., "Deep Learning is Effective for Classifying Normal versus Age-Related Macular Degeneration OCT Images," Ophthalmology Retina, vol. 1, No. 4, Jul.-Aug. 2017, pp. 322-327.
Lee, et al., "Deep-learning based, automated segmentation of macular edema in optical coherence tomography," Biomedical Optics Express, vol. 8, No. 7, Jul. 2017, pp. 3440-3448.
Lee, et al., "Generating retinal flow maps from structural optical coherence tomography with artificial intelligence," Scientific Reports, vol. 9, No. 5694, Apr. 2019, 11 pages.
Litjens, et al., "A survey on deep learning in medical image analysis," Medical Image Analysis, arXiv, vol. 42, Jun. 2017, 39 pages.
Liu, et al., "Extended axial imaging range, widefield swept source optical coherence tomography angiography," Journal of Biophotonics, vol. 10, No. 11, Nov. 2017, 20 pages.
Long, et al., "Fully Convolutional Networks for Semantic Segmentation," Proceedings of the IEEE Conference on Computer Vision and Pattern Recognition, vol. 39, No. 4, Jun. 2015, pp. 3431-3440.

(56) References Cited

OTHER PUBLICATIONS

Nesper, et al., "Quantifying Microvascular Abnormalities With Increasing Severity of Diabetic Retinopathy Using Optical Coherence Tomography Angiography," IOVS, vol. 58, Oct. 2017, pp. 307-315.
Ng, "Feature selection, L1 vs. L2 regularization, and rotational invariance," retrieved on Jul. 7, 2021 at «http://cseweb.ucsd.edu/~elkan/254spring05/Hammon.pdf», Proceedings of the Twenty-First International Conference on Machine Learning, Apr. 2005, 20 pages.
Niki, et al., "Distribution of capillary nonperfusion in early-stage diabetic retinopathy," Ophthalmology, vol. 91, No. 12, Dec. 1984, pp. 1431-1439.
PCT Search Report and Written Opinion mailed Jul. 22, 2020 for PCT Application No. PCT/US20/29941, 8 pages.
Ronneberger, et al., "U-Net: Convolutional Networks for Biomedical Image Segmentation," arXiv,, May 2015, pp. 234-241 (8 pages).
Roy, et al., "ReLayNet: retinal layer and fluid segmentation of macular optical coherence tomography using fully convolutional networks," Biomedical Optics Express, vol. 8, No. 8, Aug. 2017, pp. 3627-3642.
Schottenhamml, et al., "An automatic, intercapillary area based algorithm for quantifying diabetes related capillary dropout using OCT angiography," Retina, vol. 36, No. 1, Dec. 2016, 15 pages.
Simonyan, et al., "Very Deep Convolutional Networks for Large-Scale Image Recognition," arXiv, Apr. 2015, 14 pages.
Spaide, et al., "Optical coherence tomography angiography," Progress in Retinal and Eye Research, vol. 64, Dec. 2017, pp. 1-55.
Srinivasan, et al., "Fully automated detection of diabetic macular edema and dry age-related macular degeneration from optical coherence tomography images," Biomedical Optics Express, vol. 5, No. 10, Oct. 2014, pp. 3568-3577.
Szegedy, et al., "Inception-v4, Inception-ResNet and the Impact of Residual Connections on Learning," Proceedings of the Thirty-First AAAI Conference Artificial Intelligence, Feb. 2017, pp. 4278-4284.
Ting, et al., "Artificial intelligence and deep learning in ophthalmology," British Journal of Ophthalmol, vol. 103, Feb. 2019, pp. 167-175.
Treder, et al., "Automated detection of exudative age-related macular degeneration in spectral domain optical coherence tomography using deep learning," Graefe's Archive for Clinical and Experimental Ophthalmology, vol. 256, Feb. 2018, pp. 259-265.
Venhuizen, et al., "Deep learning approach for the detection and quantification of intraretinal cystoid fluid in multivendor optical coherence tomography," Biomedical Optics Express, vol. 9, No. 4, Mar. 2018, pp. 1545-1569.
Venhuizen, et al., "Robust total retina thickness segmentation in optical coherence tomography images using convolutional neural networks," Biomedical Optics Express, vol. 8, No. 7, Jun. 2017, pp. 3292-3316.
Wang, et al., "Automated detection of preserved photoreceptor on optical coherence tomography in choroideremia based on machine learning," Journal of BIOPhotonics, 11(5):e201700313, May 2018, 20 pages.
Wang, et al., "Automated detection of photoreceptor disruption in mild diabetic retinopathy on volumetric optical coherence tomography," Biomedical Optics Express, vol. 8, No. 12, Dec. 2017, pp. 5384-5398.
Wessel, et al., "Peripheral retinal ischaemia, as evaluated by ultra-widefield fluorescein angiography, is associated with diabetic macular oedema," British Journal of Ophthalmology, vol. 96, No. 5, Mar. 2012, pp. 694-698.
Zhang, et al., "A Novel Strategy for Quantifying Choriocapillaris Flow Voids Using Swept-Source OCT Angiography," Investigative Ophthalmology & Visual Science, vol. 59, Jan. 2018, pp. 203-211.
Zhang, et al., "Advanced image processing for optical coherence tomographic angiography of macular diseases," Biomedical Optics Express, vol. 6, No. 12, Dec. 2015, pp. 4661-4675.
Zhang, et al., "Automated Quantification of Nonperfusion in Three Retinal Plexuses Using Projection-Resolved Optical Coherence Tomography Angiography in Diabetic Retinopathy," Investigative Ophthalmology & Visual Science, vol. 57, No. 13, Oct. 2016, pp. 5101-5106.
Zhang, et al., "Projection-resolved optical coherence tomographic angiography," Biomedical Optics Express, vol. 7, No. 3, Mar. 2016, pp. 816-828.
Guo, et al., "MEDnet, a Neural Network for Automated Detection of Avascular Area in OCT Angiography", Biomedical Optics Express, vol. 9, No. 11, Nov. 1, 2018, pp. 5147-5158.
Hassan, et al., "Deep Learning Based Automated Extraction of Intra-Retinal Layers for Analyzing Retinal Abnormalities", Sep. 2018, IEEE, 20th International Conference on e-Health Networking, Applications and Services, Healthcom, 5 pages.
Office Action for U.S. Appl. No. 16/858,384, dated Jul. 7, 2021, Jia, "Detecting Avascular Areas Using Neural Networks", 15 pages.
Prentasic, et al., "Segmentation of the foveal microvasculature using deep learning networks," Journal of Biomedical Optics, vol. 21, No. 7, Jul. 2016, pp. 075008-1-075008-7.
Eladwi, et al., "Early diabetic retinopathy diagnosis based on local retinal blood vessel analysis in optical coherence tomography angiography (OCTA) images", Medical Physics 45 (10), Oct. 2018, pp. 4582-4599.
International Preliminary Report on Patentability for PCT Application No. PCT/US2020/029941, dated Nov. 4, 2021, 7 pages.

\* cited by examiner

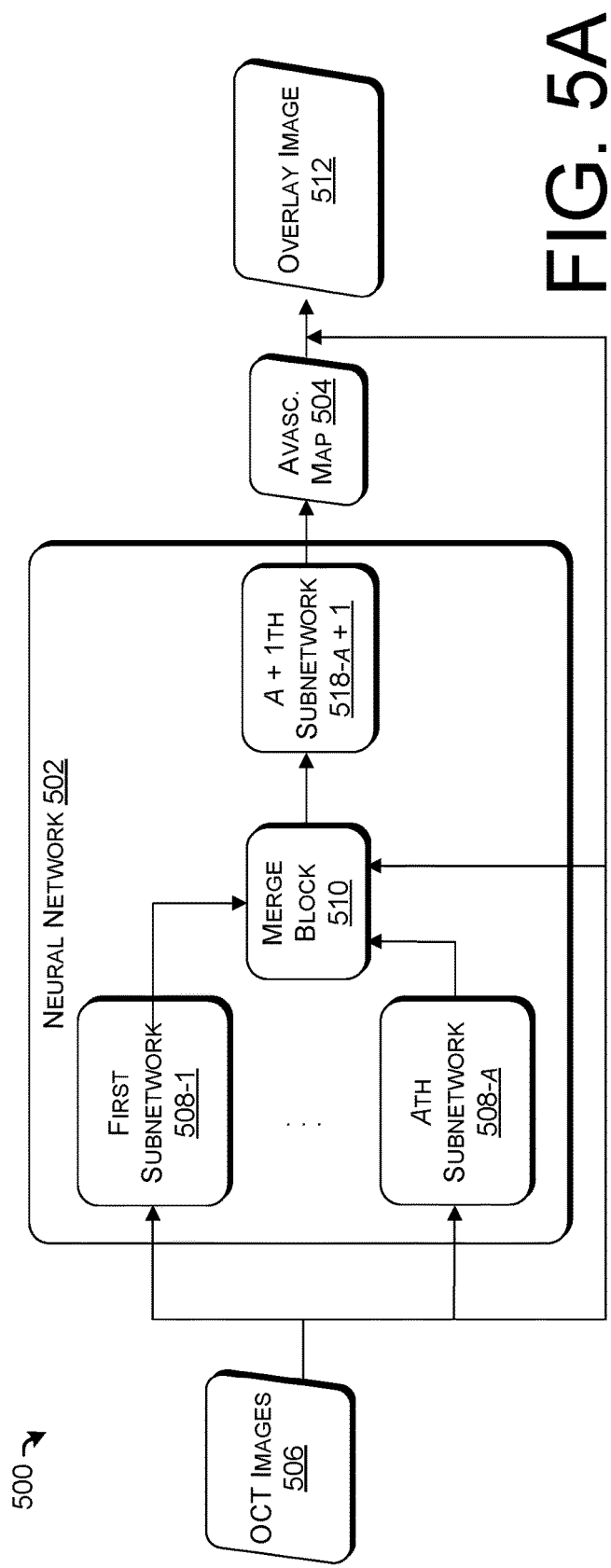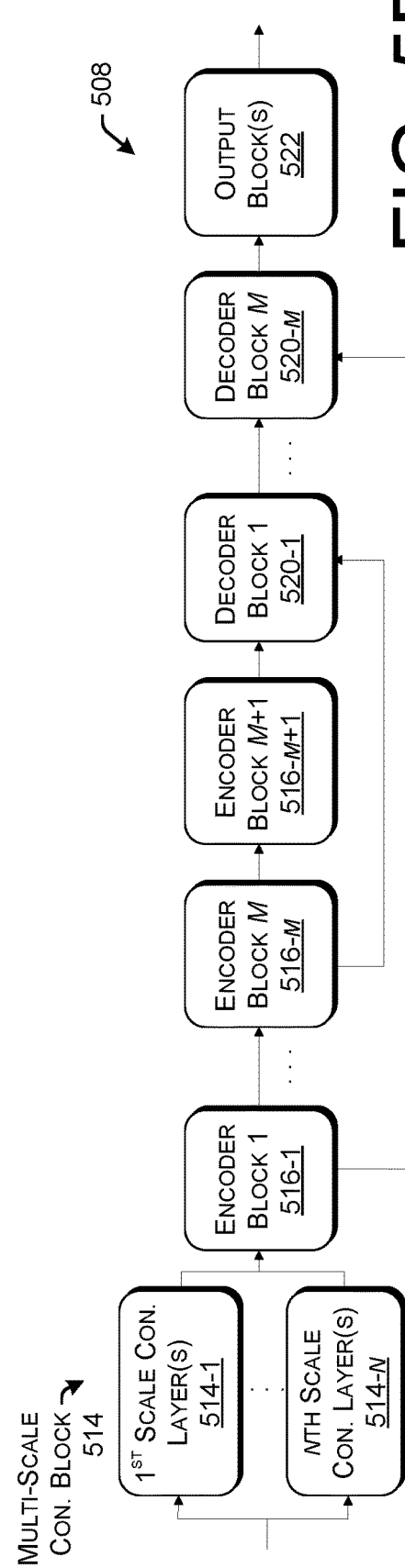

DETECTING AVASCULAR AND SIGNAL REDUCTION AREAS IN RETINAS USING NEURAL NETWORKS

CROSS-REFERENCE TO RELATED APPLICATIONS

This application is a U.S. National Phase Application based on International Patent Application No. PCT/US2020/029941 filed Apr. 24, 2020, titled "DETECTING AVASCULAR AND SIGNAL REDUCTION AREAS IN RETINAS USING NEURAL NETWORKS," which claims the priority of U.S. Provisional Application No. 62/839,349, titled "DETECTING AVASCULAR AREAS USING NEURAL NETWORKS" and filed on Apr. 26, 2019, both of which are incorporated by reference herein in their entirety.

STATEMENT REGARDING FEDERALLY SPONSORED RESEARCH

This invention was made with government support under EY027833 and DK104397 awarded by the National Institutes of Health. The government has certain rights in the invention.

TECHNICAL FIELD

This application relates to the field of medical imaging, and in particular, retinal imaging.

BACKGROUND

Retinal capillary dropout is one of the main causes of vision loss in Diabetic Retinopathy (DR) patients. With the availability of commercial Optical Coherence Tomography Angiography (OCTA) technology, ophthalmologists can acquire high quality, three-dimensional images of retinal and choroidal circulation with capillary-level detail. OCTA has several distinct advantages over fluorescein angiography: it is injection-free, faster, less expensive, obtains higher resolution, and is depth resolved, all of which indicate that it has great clinical potential for detecting and quantifying Non-Perfusion Areas (NPA). Nonetheless, this potential remains unrealized due to difficulties in correctly accounting for artifacts in OCTA images that can mar image quality and confound interpretation of data.

An NPA of the superficial capillary complex (SVC) in the retina is an important indicator of the DR stage and progression. See, e.g., Hwang et al., JAMA OPHTHALMOLOGY 97239, 929-36 (2018); Zhang et al., INVESTIGATIVE OPHTHALMOLOGY AND VISUAL SCIENCE 57, 5101-06 (2016); Hwang et al., RETINA (Philadelphia, Pa.) 35, 2371-76 (2015); & Hwang et al., JAMA OPHTHALMOLOGY 134, 1411 (2016).

Recent studies in semantic segmentation using deep Convolution Neural Networks (CNN) have greatly promoted the application of neural networks in medical image processing. See Ting et al., BRITISH JOURNAL OF OPHTHALMOLOGY, 167-175 (2018) & Litjens et al., MEDICAL IMAGE ANALYSIS 42, 60-88 (2017). In ophthalmology, CNNs can detect types of retinopathy on OCT images, like diabetic macular edema (see, e.g., Venhuizen et al., BIOMED. OPTICS EXP. 9, 1545 (2018) & Lee et al., BIOMED. OPTICS EXP. 8, 3440 (2017)), Age-related Macular Degeneration (AMD) (see, e.g., Treder et al., GRAEFE'S ARCHIVE FOR CLINICAL AND EXPERIMENTAL OPHTHALMOLOGY 256, 259-265 (2018) & Lee et al., OPHTHALMOLOGY RETINA 1, 124-136 (2016)), or drusen (Kermany et al., CELL 172, 1122-1124.e1129 (2018)). Some researchers also tried to use CNNs to segment retinal layers on OCT images, and used the powerful feature extraction capabilities of CNNs to generate retina flow maps from structural OCT images. See, e.g., Fang et al., BIOMED. OPTICS EXP. 8, 2732-44 (2017); Devalla et al., BIOMED. OPTICS EXP. 8, 3627 (2018); Hamwood et al., BIOMED. OPTICS EXP. 9, 3049 (2018); Roy et al., BIOMED. OPTICS EXP. 8, 3627-42 (2017); Venhuizen et al., BIOMED. OPTICS EXP. 8, 3292 (2017); & Lee et al., arXiv: 1802.08925 (2018) (describing generation of retina flow maps from structural OCT images).

With the development of deep learning, many network structures with excellent feature expression ability have been proposed (e.g. U-net, ResNet, Inception, Densnet). See, e.g., He et al., FRONTIERS IN PSYCHOLOGY 4, 770-778 (2015) (describing ResNet); Szegedy et al., AAAI (2017), p. 12 (describing Inception); & Huang et al., 2017 IEEE CONFERENCE ON COMPUTER VISION AND PATTERN RECOGNITION (CVPR) (IEEE, 2017), pp. 2261-69 (describing Densnet). With reference to these state-of-the-art network structures, researchers can build networks that meet the needs of their subjects.

SUMMARY

An example system includes an output device, at least one processor, and memory. The memory stores instructions that, when executed by the at least one processor, cause the system to perform operations that include generating a filtered reflectance image of an inner portion of a retina by applying a Gaussian filter to an optical coherence tomography (OCT) image of the inner portion; generating, using a first convolutional neural network (CNN), a first output image based on the filtered reflectance image; generating, using a second CNN, a second output image based on a thickness image of the inner portion; generating a merged image by merging the first output image, the second output image, and an OCT angiography (OCTA) image of the retina, the OCTA image depicting at least a 3×3 mm$^2$ area of the retina and including at least one signal reduction area; generating, using a third CNN, an avascular map of the retina based on the merged image, the avascular map including a first group of pixels indicating at least one avascular region in the retina and a second group of pixels indicating at least one signal reduction area in the OCTA image; and causing the output device to display the avascular map overlying the OCTA image.

According to implementations, a method includes identifying a plurality of first images of a plurality of first retinas, the plurality of first images including thickness images of the first retinas, reflectance intensity maps of the first retinas, and optical coherence tomography angiography (OCTA) images of the first retinas; identifying a plurality of first avascular maps corresponding to the plurality of first images, wherein at least one of the first avascular maps a first level, a second level, and a third level, the first level indicating a vascular area in a particular one of the first images, the second level indicating an avascular area in the particular one of the first images, and the third level indicating a signal reduction area in the particular one of the first images; and training at least one convolutional neural network (CNN) based on the plurality of first images and the plurality of first avascular maps.

An example method includes generating an avascular map by inputting an inner retinal thickness map of a retina, a reflectance intensity image of the retina, and an optical coherence tomography angiography (OCTA) image of the retina into at least one convolutional neural network (CNN).

In some instances, a system includes at least one processor; and memory storing instructions. When executed by the at least one processor, the instructions cause the at least one processor to perform operations that include inputting first images into a trained neural network, the first images including a thickness image of a first retina, a reflectance intensity map of the first retina, and an optical coherence tomography angiography (OCTA) image of the first retina; and receiving a first avascular map from the trained neural network, the first avascular map corresponding to the first images. The first avascular map includes first and second levels, the first level indicating a vascular of the OCTA image and the second level indicating an avascular area of the OCTA image. The first avascular map further includes a third level, the third level indicating a signal reduction area of the OCTA image.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIGS. 5A and 5B illustrate examples of a neural network configured to generate an avascular map from at least one OCT image.

DETAILED DESCRIPTION

Figure 1:
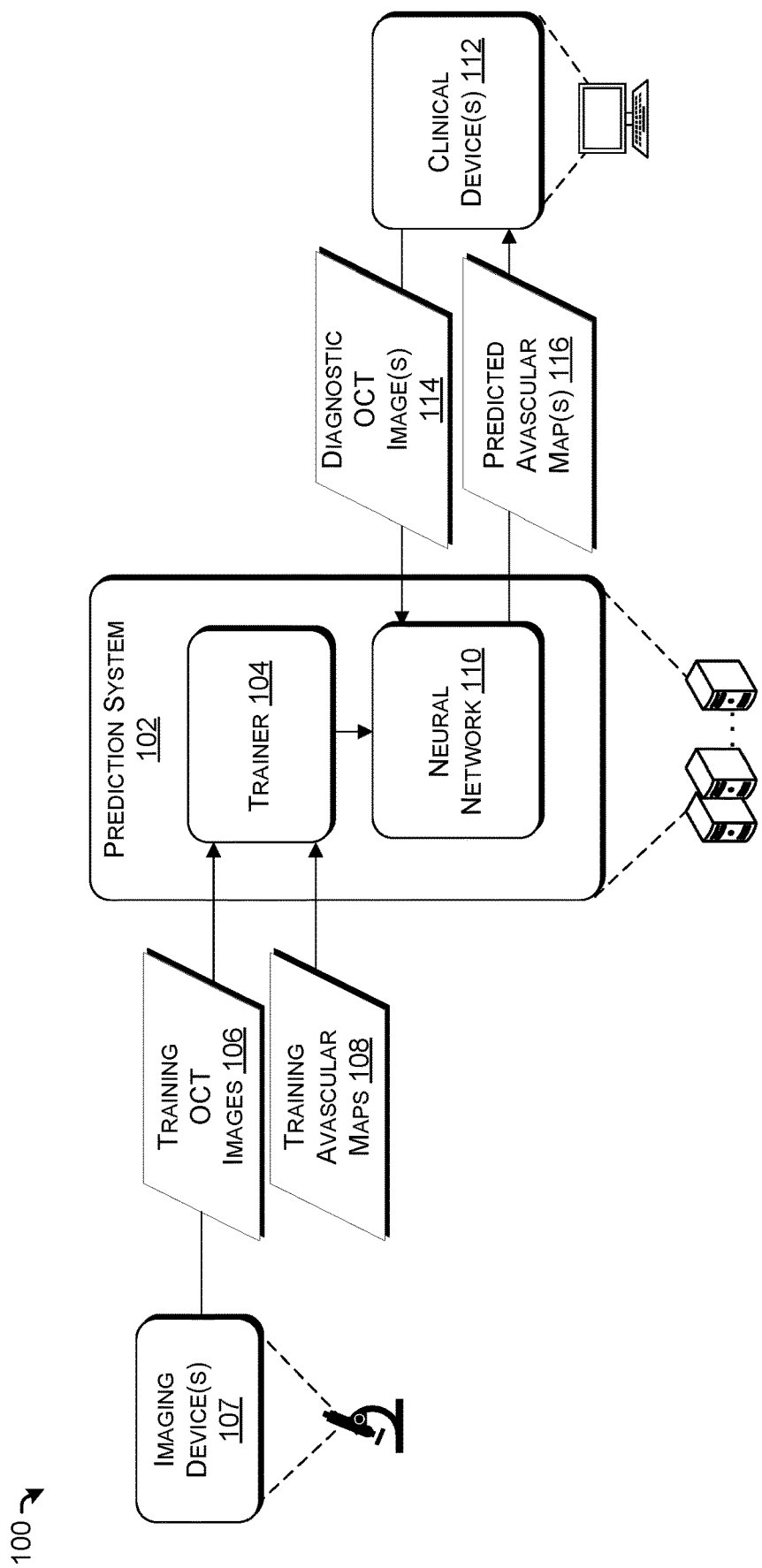
FIG. 1 illustrates an example environment for training and utilizing a neural network.

This disclosure describes systems, devices, and techniques for training neural networks to identify avascular areas of OCT images. This disclosure also describes systems, devices, and techniques for utilizing trained neural networks to identify avascular areas of OCT images. Screening and assessing DR are essential for reducing morbidity associated with diabetes. Macular ischemia is known to correlate with the severity of retinopathy. OCTA, with intrinsic contrast from blood flow motion, is well suited for quantified analysis of the avascular area, which is potentially a useful biomarker in DR.

Prior studies have demonstrated that the avascular area of the superficial capillary complex in the retina is an important indicator of DR stage and progression. See, e.g., Zhang et al., INVEST. OPHTHALMOL. VIS. SCI. 57(13), 5101-06 (2016); Hwang et al., RETINA 35(11), 2371-76 (2015); Hwang et al., JAMA OPHTHALMOL. 134(12), 1411-19 (2016); & Hwang et al., JAMA OPHTHALMOL. 136(8), 929-36 (2018). In order to accurately measure the avascular area, in certain implementations disclosed herein, OCTA flow pixels were classified properly in order to correctly identify regions with abnormal inter-vascular space. However, discriminating vascular signal in OCTA is a challenging task owing to the dependence of background flow signal on local tissue reflectivity and the confounding effects of eye motion. Camino et al., BIOMED. OPT. EXPRESS 8(6), 3053-66 (2017) & Camino et al., BIOMED. OPT. EXPRESS 7(10), 3905-15 (2016).

High-speed OCT systems (see, e.g., Liu et al., J. BIOPHOTONICS 10(11), 1464-72 (2017)) and efficient OCTA algorithms (see, e.g., Jia et al, OPT. EXPRESS 20(4), 4710-25 (2012)) have made possible the acquisition of considerably larger fields of view (3×3 $mm^2$ or more). Unfortunately, larger fields of view introduce new image processing challenges to the classification of flow pixels. For instance, 6×6 $mm^2$ OCT angiograms are more likely to contain shadows caused by vitreous floaters or pupil vignetting, and are more vulnerable to shadowing effects due to lower sampling rates. Moreover, the 6×6 $mm^2$ area encompasses vasculature on two sides of the fovea (optic disc vs temporal side) in which the normal inter-vascular space is significantly different. In order to account for these and other issues, more sophisticated detection/segmentation algorithms are described herein.

In some implementations, segmentation can be considered a pixel-wise classification problem and can be amenable to machine learning approaches. Fully Convolutional Networks (FCNs) have been proposed to transform fully connected layers in Convolutional Neural Networks (CNNs) into convolutional layers, in order to convert the network output into a heat map. See, e.g., Long et al., IEEE TRANSACTIONS ON PATTERN ANALYSIS AND MACHINE INTELLIGENCE 39(4), 3431-40 (2015). Because the encoding module can reduce the resolution of the input by a factor of 32, it can be difficult for the decoding module to produce a fine segmentation map.

To solve the loss of resolution, across-layer connections have been used in fully convolutional solutions. A successful FCN called U-net added a contracting path to capture context and a symmetric expanding path to identify the location of objects with precision. See, e.g., Ronneberger et al., MEDICAL IMAGE COMPUTING AND COMPUTER-ASSISTED INTERVENTION—MICCAI 2015, Navab et al., eds. (2015), 234-41.

Another network, known as Deeplab, can use atrous convolution kernels, which can reduce the loss of resolution but also reduce the number of trainable parameters, thereby improving segmentation accuracy. See, e.g., Chen et al., IEEE TRANS. PATTERN ANAL. MACH. INTELL. 40(4), 834-48 (2018) & Chen et al., CoRR abs/1706.05587 (2017). Other state-of-the-art network structures (see, e.g., Simonyan et al., arXiv preprint arXiv:1409.1556 (2014) (describing a neural network known as VGG); He et al., PROCEEDINGS OF THE IEEE CONFERENCE ON COMPUTER VISION AND PATTERN RECOGNITION (2016), pp. 770-78 (describing a neural network known as ResNet); & Szegedy et al., AAAI (2017), p. 12 (describing a neural network known as Inception)) as a part of semantic segmentation network can streamline the design process of network and can take the advantage of the superior performance of existing networks. For example, a neural network known as Segnet, which borrows a network structure similar to VGG, can provide an efficient semantic segmentation network. See, e.g., Badrinarayanan et al., arXiv:1511.00561 (2015).

Several other machine learning solutions have segmented pathological areas with abnormal tissue reflectance characteristics in OCT images. See, e.g., Fang et al, BIOMED. OPT. EXPRESS 8(5), 2732-44 (2017); Srinivasan et al., BIOMED. OPT. EXPRESS 5(10), 3568-37 (2014); Karri et al., BIOMED. OPT. EXPRESS 8(2), 579-592 (2017); Camino et al., BIOMED. OPT. EXPRESS 9(7), 3092-05 (2018); Wang et al., J. BIOPHOTONICS 11(5), e201700313 (2018); Wang et al., BIOMED. OPT. EXPRESS 8(12), 5384-98 (2017). The metrics based on OCTA image analysis can complement OCT for earlier assessment of ocular diseases with a vascular component, such as DR. Some researchers have built deep convolution networks capable of segmenting the foveal microvasculature on OCTA images. Prentašić et al., J. BIOMED. OPT. 21(7), 75008 (2016). However, none of these studies have proposed a network that can effectively and accurately segment vascular areas from non-vascular areas in OCT images.

In this disclosure, various deep learning solutions for segmenting avascular areas in OCTA of DR are disclosed. Particular implementations utilize a novel network design that includes a Multi-scaled Encoder-Decoder neural network, version 2 (MEDnet-V2) to detect non-perfusion areas in 6×6 mm$^2$ and in ultra-wide field retinal angiograms. Avascular areas can be effectively detected in DR subjects of various disease stages as well as in the foveal avascular zone of healthy subjects.

Particular neural networks described herein provide accurate diagnoses of avascularity using relatively inexpensive and non-toxic imaging modalities, such as structural OCT and OCTA. In some examples demonstrated herein, neural networks can predict avascular areas based on OCTA images and OCT reflectance images with an accuracy of 81.88%. This level of accuracy is comparable to previous work, in which avascular areas were predicted from high-quality 3×3 mm OCTA high-definition scans. See, e.g., Zhang et al., INVEST OPHTHALMOL VIS SCI, 57(13), 5101-06 (2016). However, unlike the previous work, implementations of the present disclosure were able to achieve this high accuracy without excluding low-quality scans for training. See id.

According to various implementations, a neural network can be trained using OCT images with known avascular regions. The avascular regions of the training images may be manually segmented (i.e., defined) by one or more experts. In some cases, the neural network can be trained using both OCT reflectance images and OCTA images of the same retinas. When the neural network is trained using OCT images depicting a wide variety of disease progressions, the accuracy of the trained neural network can be enhanced.

Once trained, the neural network can be used to accurately predict avascular regions of new OCT images. When a particular OCT image is input into the trained neural network, the trained neural network can output a map of a predicted avascular region corresponding to the particular OCT image. According to some implementations, the neural network may output a probability map including multiple elements that respectively correspond to the likelihood that a given pixel in the particular OCT image depicts a particular area being segmented, such as an area of vascularity, an area of avascularity, or an area of signal reduction. In some cases, each element of the probability map includes three different probabilities, corresponding respectively to the probabilities that the corresponding pixel depicts a vascular area, an avascular area, or a signal reduction area.

In certain implementations, the avascular map can be generated by selecting, for each pixel, the area corresponding to the highest probability. For example, a given pixel in an OCT image may correspond to three probability values in the probability map. A first probability value may represent a probability that the pixel is part of a vascular area. A second probability value may represent a probability that the pixel is part of an avascular area. A third probability value may represent a probability that the pixel is part of a signal reduction area. If the first probability value is the highest among the first through third probability values, an avascular map may be generated to include a pixel (corresponding to the given pixel in the OCT image) that indicates the given pixel is part of the vascular area.

In some cases, a map of the predicted avascular region can be generated by selecting a probability threshold. For example, if the second probability is greater than a threshold of 50%, the pixel in the avascular map may be defined as indicating the given pixel is part of the avascular area. In some cases, a clinical device can display the map indicating the predicted avascular region overlaid with the particular OCT image. Accordingly, clinicians can easily identify areas of clinical interest in particular OCT images.

In particular implementations, a neural network for identifying avascular areas of OCT images can include multiple convolution blocks arranged in series and/or parallel. Each of the convolution blocks may correspond to at least one parameter that can be defined by training the neural network. In some instances, the neural network can include a multi-scale block that includes multiple convolution blocks arranged in parallel. The convolution blocks in the multi-scale block may apply convolution kernels with different dilation rates. The neural network may further include at least one merge block that can merge the outputs of the parallel convolution blocks in the multi-scale block. A merge block may concatenate the outputs of the parallel convolution blocks along a depth axis. Accordingly, the multi-scale block can enable the neural network to accurately process OCT images taken at various angles and scales. Example neural networks described herein may also include one or more batch normalization blocks. The batch normalization blocks can reduce overfilling during training.

Various implementations disclosed herein also relate to neural networks that can accurately produce avascular maps from OCT images with noise and artifacts. Previously, OCTA imaging has been seriously hindered by the inability of automated algorithms to correctly manage complications introduced by artifacts and noise. OCTA is an extremely powerful technology in terms of the vascular detail it can capture (i.e., it obtains high resolution, volumetric data), but even in the best circumstances it is prone to imaging artifacts. See Spaide et al., PROGRESS IN RETINAL AND EYE RESEARCH 64, 1-55 (2018). This drawback is exacerbated for scans of DR eyes, which are often rich in complications but poor in quality. Avascular maps then, though an excellent indicator of DR progression, will ultimately remain clinically under-utilized until algorithms can distinguish true NPA can be correctly distinguished from dropout due to shadowing artifact. The problem is relatively intractable for traditional image analysis techniques.

Previously published results that relied on such approaches have then either ignored complications from shadowing artifacts (see, e.g., Schottenhamml et al., RETINA (Philadelphia, Pa.) 36, S93 (2016); Agemy et al., RETINA 35, 2353-2363 (2015); & Nesper et al., INVESTIGATIVE OPHTHALMOLOGY & VISUAL SCIENCE 58, B10307-610315 (2017)) or required manual correction (see, e.g., Alibhai et al., RETINA (Philadelphia, Pa.) (2018)). Unlike previous approaches, various implementations of the present disclosure utilize neural networks capable of automatically reducing the effects of noise or artifacts (e.g., floater shadows, pupil vignetting, defocus, etc.) in classifying non-vascular areas in OCT images. According to certain examples, the neural network can output an avascular map that identifies likely signal artifacts as well as avascular areas.

In some implementations, a neural network capable of outputting avascular maps that identify signal artifacts and avascular areas can include multiple subnetworks. Some of these subnetworks can accept various OCT image inputs, such as OCTA images, OCT reflectance intensity maps, and retinal thickness images. In some cases, different types of OCT images are independently processed by subnetworks in the neural network. For instance, OCT reflectance intensity maps can be input into a first subnetwork and retinal thickness images can be input into a second subnetwork. In certain examples, the outputs of the first and second subnetworks can be merged together. According to particular implementations, the merged outputs of various subnetworks can be fed into another subnetwork of the neural network.

Certain implementations of neural networks disclosed herein can detect non-perfusion with high accuracy, specificity, and sensitivity. In some cases described herein, neural networks were able to identify non-perfusion areas with an accuracy of at least 95%, at least 98%, or at least 99%. In certain examples, neural networks were able to identify non-perfusion areas with a specificity of at least 98% or 99%. In particular instances, neural networks were able to identify non-perfusion areas with a sensitivity of at least 75%, at least 89%, at least 92%, at least 93%, or at least 95%.

In particular implementations, the impact of signal reduction in OCTA images can be reduced or eliminated. Accordingly, avascular areas can be measured and quantified accurately using OCTA images. These measurements can be objective, repeatable, and reproduceable.

Certain implementations use deep-learning based neural networks to determine avascular areas. These neural networks can utilize real-world complex clinical data, including relatively low-quality scans, to accurately assess nonperfusion. Accordingly, a large amount of data can be used to train the neural networks and to assist with diagnosis. According to particular implementations, both OCT-based reflectance images and OCTA images can be used to train neural networks. Using this variety of input data, neural networks can classify three categories in the images. These three categories can include vascular (i.e., perfusion) areas, avascular (i.e., nonperfusion) areas, and signal reduction areas. In some implementations, composited multi-scaled encoder-decoder networks and subnetworks can be utilized. In some cases, composited multi-scaled avascular areas can be extracted using these networks and subnetworks. Various implementations relate to neural networks that utilize multi-Gaussian filtered inner retinal reflectance slabs (i.e., reflectance intensity images). The neural networks can be trained using these slabs. The slabs can be used to suppress the effect of shadowing artifacts caused by vitreous floaters, vignetting, defocus, and other sources of noise, on the neural networks (e.g., on training and utilizing the neural networks).

In certain instances, inner retinal thickness maps can be used to train neural networks designed to determine avascular areas in OCT images. The thickness maps can suppress the effect of low reflectance from foveal avascular zones depicted in OCTA images, in some cases. Various implementations described herein provide improvements to the technical field of medical imaging. In particular examples, a neural network can automatically generate avascular maps based on OCT images. These avascular maps can provide clinicians without specialized training with the opportunity to accurately diagnose complications of DR. In some cases, the avascular maps can be displayed overlying OCT images.

In certain instances, accurate avascular maps can be generated without requiring Fluorescein Angiography (FA). Accordingly, the administration of dyes and/or contrast agents can be avoided, thereby saving time and cost. In addition, patient discomfort due to the administration of the dyes and/or contrast agents can be avoided.

In addition, various implementations described herein provide novel neural networks that are particularly effective at generating avascular maps from OCT images. These neural networks include a novel arrangement of functions that can accurately perform vascular segmentation on OCT images, such as OCTA images.

As used herein, the term "OCT image," and its equivalents, can refer to any image that is derived from OCT data. For instance, an OCT image can be an OCT reflectance image (e.g., a filtered and/or unfiltered OCT reflectance image), an OCTA image, a thickness image (also referred to as a "retinal thickness image"), or a combination thereof. In some cases, an OCT image referred to herein can depict a Superficial Vascular Complex (SVC) of a retina.

As used herein, the term "segmentation," and its equivalents, can refer to a process of defining an image into different areas or regions. For instance, a segmentation method may determine vascular or avascular regions in OCT images. In some cases, segmentation can be used to identify signal reduction areas in OCT images. An area or region can include one or more pixels.

As used herein, the terms "vascular," "perfusion," and the like can refer to an area of an image that depicts vasculature. In some cases, a perfusion area can refer to an area that depicts a blood vessel or another type of vasculature.

As used herein, the terms "avascular," "nonperfusion," and the like can refer to an area of an image that does not depict vasculature. In some cases, a nonperfusion area can refer to an area between blood vessels or other types of vasculature.

As used herein, the term "signal reduction area," or its equivalents, can refer to an area of an image that depicts noise or some other reduction of image quality. For instance, a signal reduction area in an OCT image can correspond to areas of pupil vignetting, floater shadows, defocus, or a combination thereof.

As used herein, the term "avascular map" can refer to a map of avascular areas in an image of a retina (e.g., an OCTA image). In some cases, an avascular map can further indicate vascular areas in the image and/or signal reduction areas in the image. An avascular map used in training a neural network (e.g., an avascular map based on assessments by one or more experts) can be further referred to as "ground truth."

As used herein, the terms "blocks," "layers," and the like can refer to devices, systems, and/or software instances (e.g., virtual machine (VM) instances) that generates an output by apply an operation to an input. A "convolutional block," for example, can refer to a block that applies a convolution operation to an input (e.g., an image). For the purposes of this discussion, each convolution layer and/or convolution block within this disclosure may include a batch normalization layer and/or an activation (e.g., a ReLU) layer. When a first block is in series with a second block, the first block may accept an input, generate an output by applying an operation to the input, and provide the output to the second block, wherein the second block accepts the output of the first block as its own input. When a first block is in parallel with a second block, the first block and the second block may each accept the same input, and may generate respective outputs that can be provided to a third block. In some examples, a block may be composed of multiple blocks that are connected to each other in series and/or in parallel. In various implementations, one block may include multiple layers. In some cases, a block can be composed of multiple neurons. As used herein, the term "neuron," or the like, can refer to a device, system, and/or software instance (e.g., VM instance) in a block that applies a kernel to a portion of an input to the block.

As used herein, the term "kernel," and its equivalents, can refer to a function, such a filter, performed by a neuron on a portion of an input to a block. A neuron may have a "receptive field," which can define an outer edge of the portion of the input to which a neuron applies a kernel. Some examples of a receptive field can include a 2×2 pixel area, a 3×3 pixel area, a 4×4 pixel area, or the like.

As used herein, the term "pixel," and its equivalents, can refer to a value that corresponds to an area or volume of an image. In a grayscale image, the value can correspond to a grayscale value of an area of the grayscale image. In a color image, the value can correspond to a color value of an area of the color image. In a binary image, the value can correspond to one of two levels (e.g., a 1 or a 0). The area or volume of the pixel may be significantly smaller than the area or volume of the image containing the pixel.

As used herein, the terms "dilation rate," "dilation level," and the like can refer to a scaling factor between the receptive field of a neuron and an output of the neuron. For instance, if a neuron has a receptive field corresponding to a 3×3 pixel area and outputs a 3×3 pixel area, the dilation rate of the neuron is 1. If a receptive field of a neuron corresponds to a larger area than the output of the neuron, the neuron may have a dilation rate of greater than 1.

Particular implementations of the present disclosure will now be described with reference to FIGS. 1-11. FIG. 1 illustrates an example environment 100 for training and utilizing a neural network. A prediction system 104 may include a trainer 104. The trainer 104 can receive multiple training OCT images 106. In some cases, the training OCT images 106 can include OCTA images (also referred to as "OCT angiograms"), OCT reflectance images, filtered reflectance images, thickness maps, or any combination thereof. In some examples, the training OCT image(s) 106 can be captured by at least one imaging device 107. The imaging device(s) 107 can include an OCT reflectance imaging device, at least one OCT angiography device, a combination thereof, or the like. According to particular examples, the training OCT image(s) 106 can include images captured by multiple, different devices. In some cases, the imaging device 107 is configured to obtain multiple B-scans of a single retina.

According to various implementations described herein, multiple OCT images (e.g., OCTA images, OCT reflectance images, thickness images, etc.) of the same retina can be obtained based on a volumetric scan of the retina. In some examples, various (e.g., hundreds of) B-scans of the retina can be obtained via an OCT imaging system within the imaging device(s) 107. Each B-scan may correspond to a two-dimensional image that includes multiple (e.g., hundreds of) A-lines. The B-scans may be obtained over a relatively large field of view, such as an area of at least 3×3 mm$^2$ (e.g., a 3×3 mm$^2$ area, a 6×6 mm$^2$ area, or the like) The area may be perpendicular and/or cross a direction that crosses the layers of the retina. The B-scans of the retina may be referred to as "volumetric data" of the retina. The OCTA image can be generated from the volumetric data using, for instance, the Split Spectrum Amplitude Decorrelation Angiography (SSADA) algorithm or some other suitable OCTA image generation technique. See Jia et al., OPT. EXPRESS 20(4), 4710-25 (2012).

In some cases, the OCTA image and the OCT reflectance image may depict one or more layers of the retina. In various examples described herein, an OCTA image and an OCT reflectance image may depict a Superficial Vascular Complex (SVC) of a retina. For example, layers within the retina depicted in the volumetric data can be segmented, e.g., using a graph search method. See Zhang et al., BIOMED. OPT. EXPRESS 6(12), 4661-75 (2015). The OCTA image and the OCT reflectance image may be generated from a slab of the volumetric data extending between two of the segmented boundaries of the layers of the retina. The slab, for instance, may represent the inner retina. In some implementations, the OCT reflectance image can be generated by obtaining an average image of the slab in a depth direction (e.g., a direction crossing the retinal boundaries). According to some implementations, the OCTA image can be generated by obtaining a maximum projection or a mean projection of the slab in the depth direction. In some cases, the thickness image can be generated by identifying the thickness of the slab in a direction perpendicular to the field of view.

The trainer 104 may further receive multiple training avascular maps 108. In various implementations, the training avascular maps 108 correspond to the training OCT images 106. In some examples, each avascular map among the training avascular maps 108 may correspond to one OCT angiogram, one OCT reflectance image, and one thickness image in the training OCT images 106. An image may "correspond" to another image if it depicts and/or is derived from the same subject (e.g., the same retina).

In particular implementations, the avascular maps 108 may be generated by one or more experts. For instance, an expert may select individual pixels in an OCT image (e.g., an OCTA image) that correspond to avascular areas in the OCT image, and an avascular map corresponding to the selected pixels in the OCT image may be generated. The expert may further indicate signal reduction areas in the OCT image. In some cases, the avascular map may have the same dimensions (i.e., the same number of pixels) as the OCT image. The avascular map may be a binary image, wherein each of the selected pixels corresponds to one level (e.g., 1) and each of the unselected pixels corresponds to another level (e.g., 0). In some cases, the avascular map may include a third level indicating one or more signal reduction areas within the OCT image. For instance, the avascular map may have three levels, wherein a first set of selected pixels corresponding to the avascular areas has a first value (e.g., 0), a second set of selected pixels corresponding to the signal reduction areas has a second value (e.g., 1), and a third set of pixels has a third value (e.g., 2).

In some cases, multiple experts may have different opinions on whether a given pixel in an OCT image depicts an avascular region. According to particular implementations, a majority vote of the experts may be used to determine whether the pixel is defined as an avascular region or a vascular region for the purposes of the final avascular map. For example, if there are three experts, two experts believe a pixel in an OCT image depicts a vascular region, one expert believes the pixel depicts an avascular region, a corresponding pixel in an avascular map may be defined as a vascular region. Similarly, a majority vote of the experts can be used to confirm a signal reduction area within an OCT image.

The trainer 104 may use the training OCT images 106 and the training avascular maps 108 to train a neural network 110. The neural network 110 may be trained to accept an OCT image as an input and output an avascular map corresponding to the OCT image. In various implementations, the neural network 110 may include multiple layers that can perform various operations on input OCT images. In particular implementations, at least one of the layers may perform convolution operations, cross-correlation operations, batch normalization operations, pooling operations, or the like, on various sections of the input images. The layers may be connected to each other in series, in parallel, or both.

According to various implementations, the neural network 110 may include multiple subnetworks. In some cases, each of the subnetworks may include the same or similar architecture. In some cases, a first subnetwork can receive a first type of OCT image (e.g., a thickness map) as an input and a second subnetwork can receive a second type of OCT image (e.g., a reflectance intensity image) as an input, wherein each of the first and second networks may generate respective outputs. In some cases, one of the subnetworks may receive a merged image based on a combination of at least one OCT image (e.g., an OCTA image) and/or at least one output from another subnetwork (e.g., the outputs of the first and second subnetworks). At least one of the subnetworks may have a U-net-like architecture in some cases. For example, an example subnetwork may include decoder blocks that receive the outputs of encoder blocks through across-layer connections, which allows the resolution of the output to be preserved and improves stabilization in the training phase. That is, the example subnetwork may include across-layer connections.

In particular examples, the neural network 110 may include at least one convolutional neural network (CNN) including multiple convolutional layers. For instance, each subnetwork may include a CNN. A convolutional layer may include multiple neurons. Each neuron may individually perform an operation on a segment of an input image to the layer. The area of the segment may relate to a receptive field and a dilation rate of the neuron. In some implementations, the neuron may convolve (or cross-correlate) the segment with a filter. In some examples, at least one filter can be a Gaussian filter. Each filter can include at least one parameter that can affect the output of the corresponding neuron. In particular examples, each filter can be represented by a matrix that can include multiple values arranged in at least one row and at least one column. According to various implementations, the trainer 104 may train the neural network 110 by optimizing parameters of neurons in the layers using the training OCT images 106 (e.g., OCT reflectance images, OCTA images, and thickness images) and the training avascular maps 108. In some cases, each filter can include multiple values respectively corresponding to multiple parameters that can be optimized individually. In certain examples, each filter corresponds to a single scaling factor that can apply to all values in the filter.

In some examples, the trainer 104 may vary the parameters of the neurons of the neural network 110, input at least one of the training OCT images 106 into the neural network 110, and then compare the outputs of the neural network 110 to at least one of the corresponding training avascular maps 108. The trainer 104 may determine optimized parameters of the neural network 110 by optimizing a loss function. In some cases, the loss may be the sum of the mean square error and L2 regularization loss. For example, the trainer 104 may apply the following Equations (1)-(3), in order to determine the parameters:

$$E = \frac{1}{N}\sum_{i=1}^{N}(y_i - \hat{y}_i)^2 \quad (1)$$

$$R = \sum_{i=1}^{P} w_i^2 \quad (2)$$

$$T = E + R \quad (3)$$

wherein E is the mean square error, N is the number of samples in a training batch, y is the label, $\hat{y}$ is the predicted value, w is weight factor of the model, ρ is the total number of weight factor of the model, R is L2 regularization loss and T is the total loss. Upon applying all of the training images 106 and all of the training avascular maps 108 to the neural network 110, the trainer 104 may determine a final set of optimized parameters for the neural network 110. Using the optimized parameters, the neural network 110 may be configured to accurately predict the avascular maps of new OCT images input into the neural network 110.

As illustrated in FIG. 1, at least one clinical device 112 may transmit at least one diagnostic OCT image 114 to the prediction system 102. In some examples, the diagnostic OCT image(s) 114 can be captured by at least one OCT reflectance imaging device, at least one OCT angiography device, a combination thereof, or the like. The device(s) used to capture the diagnostic OCT image(s) 114 may be part of, or in communication with, the clinical device(s) 112. In certain implementations in which the training OCT images 106 were captured by different devices, the device(s) used to capture the diagnostic OCT image(s) 114 may include multiple, different devices. In some cases, the same device(s) (e.g., the imaging device(s) 107) used to capture the training OCT images 106 are used to capture the diagnostic OCT image(s) 114. In some cases, the diagnostic OCT image(s) 114 may include an OCT reflectance image of a retina of a subject, an OCTA image of the retina, and a thickness image of the retina. The diagnostic OCT image(s) 114 can be obtained based on multiple B-scans of the retina, using similar techniques described above with reference to the training OCT images 106.

The diagnostic OCT image(s) 114 may be input into the neural network 110, which may utilize the optimized parameters. In response, the neural network 110 may output at least one predicted avascular map 116 corresponding to the diagnostic OCT image(s) 114. The prediction system 102 may transmit the predicted avascular map(s) 116 to the clinical device(s) 112. In some examples, the prediction system 102 may cause the clinical device(s) 112 to display the predicted avascular map(s) 116. For instance, the prediction system 102 may cause the clinical device(s) 112 to display the diagnostic OCT image(s) 114 overlaid with the predicted avascular map(s) 116. By displaying the predicted avascular map(s) 116, the clinical device(s) 112 may enable at least one clinician (e.g., a physician) to easily and accurately assess whether the diagnostic OCT image(s) 114 depict at least one eye with abnormal avascular regions that indicate complications of DR. In some implementations, the prediction system 102 may be hosted on one or more devices (e.g., servers) that are located remotely from the clinical device(s) 112. For example, the prediction system 102 may receive and evaluate diagnostic OCT images 114 from multiple clinical devices 112 located in various locations (e.g., various healthcare facilities).

According to certain implementations, the prediction system 102 and/or the clinical device(s) 112 may interface with an electronic medical record (EMR) system (not illustrated). The diagnostic OCT image(s) 114, predicted avascular map(s) 116, information about the diagnostic OCT image(s) 114, information about the predicted avascular map(s) 116, and the like, may be stored and/or accessed in memory stored at the EMR system.

In various implementations, at least one of the prediction system 102, the trainer 104, the neural network 110, or the clinical device(s) 112 may include at least one system (e.g., a distributed server system), at least one device, at least one software instance (e.g., a VM) hosted on system(s) and/or device(s), or the like. For instance, instructions to execute at least one of the prediction system 102, the trainer 104, the neural network 110, or the clinical device(s) 112 may be stored in memory. The instructions may be executed, in some cases, by at least one processor.

According to various examples, at least one of the training OCT image(s) 106, the training avascular maps 108, the diagnostic OCT image(s) 114, or the predicted avascular map(s) 116 may include data packaged into at least one data packet. In some examples, the data packet(s) can be transmitted over wired and/or wireless interfaces. According to some examples, the data packet(s) can be encoded with one or more keys stored by at least one of the prediction system 102, the trainer 104, the neural network 110, or the clinical device(s) 112, which can protect the data paged into the data packet(s) from being intercepted and interpreted by unauthorized parties. For instance, the data packet(s) can be encoded to comply with Health Insurance Portability and Accountability Act (HIPAA) privacy requirements. In some cases, the data packet(s) can be encoded with error-correcting codes to prevent data loss during transmission.

Figure 2:
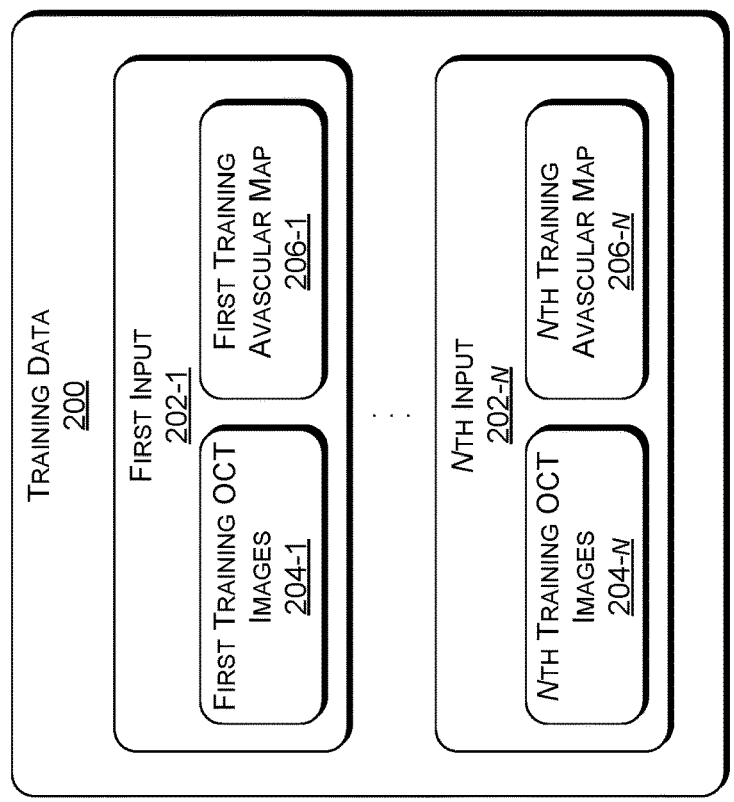
FIG. 2 illustrates an example of data used to train a neural network.

FIG. 2 illustrates an example of training data 200 used to train a neural network. In some implementations, the training data 200 may include the training OCT images 106 and the training avascular maps 108 described above with reference to FIG. 1. The training data 200 may include first to nth training OCT images 204-1 to 204-n and first to nth training avascular maps 206-1 to 206-n, which can be arranged into first to nth inputs 202-1 to 202-n, wherein n is a positive integer. In some examples, at least one of the inputs 202-1 to 202-n may include multiple training OCT images, such as an OCT reflectance image, an OCTA image, and a thickness image. For example, the first training OCT image(s) 204-1 may include an OCT reflectance image, an OCTA image, and a thickness image of the same eye.

According to various implementations, the first to nth training OCT images 204-1 to 204-n may include images taken of multiple eyes, images depicting multiple levels of disease progression, and/or images taken from multiple different devices. The multiple eyes may correspond to multiple different levels of disease progression of nonproliferation and/or DR. For example, the multiple eyes may include healthy eyes, eyes with non-proliferative DR (NPDR), eyes with mild DR, eyes with severe DR, and the like.

In various examples, the first to nth training avascular maps 206-1 to 206-n can respectively correspond to the first to nth training OCT images 204-1 to 204-n. In some examples, the first training avascular map 206-1 may be derived from the first training OCT images 204-1. For instance, one or more experts may have manually selected pixels of the first training OCT images 204-1 that correspond to avascular regions, and the selected pixels may be represented in the first training avascular map 206-1. If multiple experts provide multiple sample avascular maps of the first training OCT images 204-1, the first training avascular map 206-1 may be derived according to a pixel-wise majority vote of the experts. In some cases, the first to nth training avascular maps 206-1 to 206-n are binary images representing avascular and vascular areas of the training OCT images 204-1 to 204-n. In some examples, the first to nth training avascular maps 206-1 to 206-n may further indicate signal reduction areas (e.g., areas of pupil vignetting, floater shadows, defocus, or the like) within the first to nth training OCT images 204-1 to 204-n, which may be manually segmented by the expert(s).

According to some examples, the number and/or dimension of pixels in a given training avascular map among the first to nth training avascular maps 206-1 to 206-n may match the number and/or dimension of pixels in a corresponding training OCT image among the first to nth training OCT images 204-1 to 204-n. For example, the first training avascular map 206-1 may have the same number of rows and columns of pixels as the first training OCT images 204-1.

Figure 3:
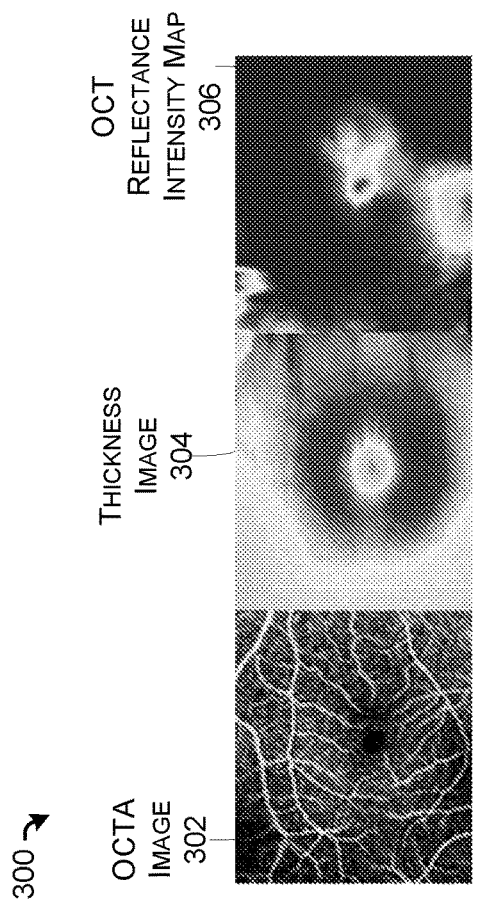
FIG. 3 illustrates an example of optical coherence tomography (OCT) images used to train a neural network.

FIG. 3 illustrates an example of OCT images 300 used to train a neural network. For example, the OCT images 300 can represent the diagnostic OCT image(s) 114 described above with reference to FIG. 1. In some cases, the OCT images 300 may correspond to the first training OCT image(s) 204-1 or the nth training OCT image(s) 204-n described above with reference to FIG. 2. As illustrated, the OCT images 300 can include an OCTA image 302, a thickness image 304, and an OCT reflectance intensity map 306. The OCT reflectance intensity map 306 may include a reflectance intensity image and/or may be based on an OCT reflectance image. The OCTA image 302, the thickness image 304, and the OCT reflectance intensity map 306 may correspond to the same scan (e.g., taken at substantially the same time of the same eye of the same patient). The OCTA image 302, the thickness image 304, and the OCT reflectance intensity map 306 may have at least one of the same field of view and the same resolution, in some cases.

In various implementations, the inclusion of the thickness image 304 and the OCT reflectance intensity map 306 can be used to reduce the impact of artifacts and other noise in the OCTA image 302. For instance, when a neural network is trained with the OCTA image 302, the thickness image 304, and the OCT reflectance intensity map 306, the thickness image 304 and the OCT reflectance intensity map 306 can reduce the influence of artifacts in the OCTA image 302 on the parameters of the neural network. In particular implementations, the thickness image 304 is generated based on a B-scan image. The B-scan can indicate a three-dimensional image of the retina, such that individual retinal layer boundaries can be determined. The retinal thickness image 304 may correspond to the thickness of the inner retina. In some cases, the reflectance intensity map 306 can be derived from an OCT reflectance image. For instance, the reflectance intensity map 306 may be generated by applying a multi-Gaussian filter on an OCT reflectance image.

Figure 4:
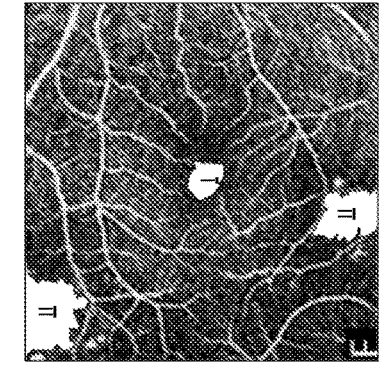
FIG. 4 illustrates an example of an avascular map corresponding to the OCT images illustrated in FIG. 3.

FIG. 4 illustrates an example of an avascular overlay image 400 corresponding to the OCT images 300 illustrated in FIG. 3. For example, the avascular overlay image 400 may correspond to an avascular map derived from the OCT images 300 and overlaid on the OCTA image 302. In some examples, the avascular map of the avascular overlay image 400 may correspond to the first training avascular map 206-1 or the nth training avascular map 206-n described above with reference to FIG. 2.

The avascular map in the overlay image 400 can be an image with three levels. The first level (e.g., corresponding to the exposed areas of the OCTA image 302) may correspond to vascular regions of the OCT images 300. The second level (e.g., corresponding to area "I" of the overlay image 400) can correspond to avascular areas depicted in the OCT images 300. The third level (e.g., corresponding to areas "II" of the overlay image 400) can correspond to signal reduction areas in the OCT images 300. The avascular map may have the same pixel dimensions as the OCTA image 302, such that it can be overlaid on the OCT image 302 in the overlay image 400.

FIG. 5A illustrates an example of an environment including a neural network 502 configured to generate an avascular map 504 from multiple OCT images 506. In some cases, the neural network 502 can correspond to the neural network 110 described above with reference to FIG. 1. The neural network 502 can include first to ath subnetworks 508-1 to 508-a, wherein a is a positive integer. The first to ath subnetworks may be arrange in parallel. In various implementations, the subnetworks 508-1 to 508-a may receive individual types of OCT images among the OCT images 506. For example, the first subnetwork 508-1 may receive a thickness image among the OCT images 506, a second subnetwork among the subnetworks 508-1 to 508-a may receive an OCT reflectance intensity map, and so on.

The first to ath subnetworks 508-1 to 508-a may individually generate outputs (e.g., output images), which are then input into a concatenation or merge block 510. In some cases, one or more of the OCT images 506 are also input into the merge block 510. For instance, the merge block 510 may also receive an OCTA image among the OCT images 506. The merge block 510 may combine the individual outputs from the subnetworks 508-1 to 508-a and/or one or more of the OCT images 506.

An output of the merge block 510 may be input into an a+1th subnetwork 518-a+1. According to various implementations, the a+1th subnetwork may output the avascular map 504. The avascular map 504 may have three levels, corresponding to a vascular area in at least one of the OCT images 506, an avascular area in at least one of the OCT images 506, and a signal reduction area in at least one of the OCT images 506.

In some implementations, an overlay image 512 can be generated based on one of the OCT images 506 and the avascular map 504. In some examples, the portions of the avascular map 504 corresponding to avascular areas and the signal reduction areas can be overlaid with an OCTA image among the OCT images 506. The overlay image 512 can indicate avascular areas in the OCT images 506 (e.g., with a first color), signal reduction areas in the OCT images 506 (e.g., with a second color), and the remaining portions correspond to vascular areas of an OCTA image.

FIG. 5B illustrates an example of a subnetwork 508, which can correspond to any of the subnetworks 508-1 to 508-a+1 described above with reference to FIG. 5A. The subnetwork 508 may be a convolutional neural network (CNN). The subnetwork 518, for example, includes a multi-scale convolution block 514, that includes first through nth scale convolution layers 514-1 to 514-n (wherein n is a positive integer); an encoder including first to m+1th encoder blocks 516-1 to 516-m+1 (wherein m is a positive integer); a decoder including first to mth decoder blocks 520-1 to 520-m, and at least one output block 522. The blocks 514 to 522 are arranged in series, parallel, or a combination thereof.

The first to nth scale convolution layers 514-1 to 514-n in the multi-scale convolution block 514 may be arranged in parallel. In some cases, the first scale convolution layer(s) 514-1 may include at least one first convolution layer applying a first dilation rate, and second scale convolution layer(s) among the first to nth scale convolution layers 514-1 to 514-n that apply a second dilation rate, which is different than the first dilation rate. In some cases, the respective outputs from the first to nth scale convolution layers 514-1 to 514-n may be merged (e.g., concatenated).

The encoder blocks 516-1 to 516-m+1 may be arranged in series and receive the merged output from the multi-scale convolution block 514. In various cases, the encoder blocks 516-1 to 516-m+1 may include multiple convolution layers. An output from the final, m+1th encoder block 516-m+1 is input into the first decoder block 512-1. In addition, the first decoder block 512-1 receives an output from the mth encoder block 516-m. The decoder block 512-1 may include a concatenation layer that concatenates the outputs from the m+1th encoder block 516-m+1 and the mth encoder block 516-m and at least one convolution layer that generates an output based on the concatenated image. Each of the first to mth encoder blocks 516-1 to 516-m may output to its proceeding encoder block and to a corresponding decoder block among the decoder blocks 520-1 to 520-m. Each of the first to mth decoder blocks 520-1 to 520-m may receive inputs from its preceeding block and a corresponding encoder block among the first to mth encoder blocks 516-1 to 516-m. The subnetwork 508 illustrated in FIG. 5B has a U-Net-like architecture. The output block(s) 522 may include one or more convolution layers that process the output from the mth decoder block 520-m to generate the output of the subnetwork 508.

According to various examples, the blocks 514 to 522 include one or more of convolutional (e.g., atrous convolutional) layers, max pooling layers, upsampling layers, concatenation (e.g., merge) layers, or batch normalization layers. Each convolution layer in the subnetwork 508 may be configured to perform a convolution and/or cross-correlation operation between a corresponding filter and an input image. Parameters defining the filter can be optimized during training. In some examples, a max pooling layer may reduce the spatial size of an input to reduce the amount of parameters and computation in the overall subnetwork. An upsampling layer may increase the spatial size of an input. A concatenation layer may concatenate multiple inputs in a depth axis. A batch normalization layer may reduce overfilling, which can make the neural network more stable during training. In some cases, additional blocks and/or layers may be included within the subnetwork 508. For instance, one or more layers (e.g., at least one convolutional layer) may preprocess the input to the subnetwork 508 before the input is processed using the multi-scale convolution block 514.

Figure 6:
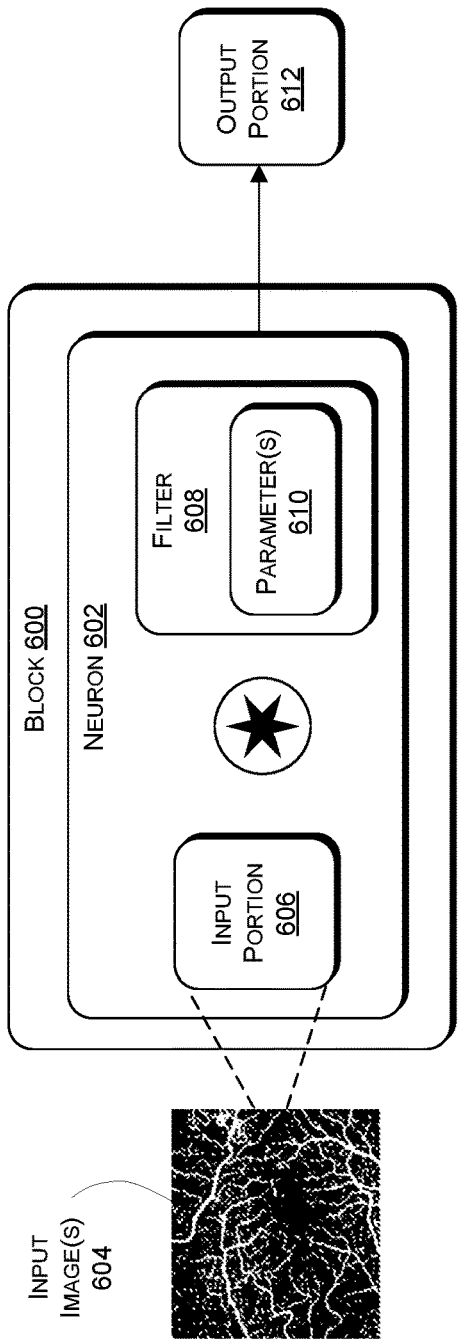
FIG. 6 illustrates an example of a convolutional block in a neural network.

FIG. 6 illustrates an example of a convolutional block 600 in a neural network. In some examples, the block 600 can be included in any of the subnetworks 508-1 to 508-a+1 and/or any of the blocks 514 to 522 described above with reference to FIGS. 5A and 5B. The convolutional block 600 may include multiple neurons, such as neuron 602. In some cases, the number of neurons may correspond to the number of pixels in at least one input image 604 input into the block 600. Although one neuron is illustrated in FIG. 6, in various implementations, block 600 can include multiple rows and columns of neurons. In particular examples, the number of neurons in the block 600 may be less than or equal to the number of pixels in the input image(s) 604. In some cases, the number of neurons in the block 600 may correspond to a stride of neurons in the block 600. In some examples in which first and second neurons are neighbors in the block 600, the stride may refer to a lateral difference in an input of the first neuron and an input of the second neuron. For example, a stride of one pixel may indicate that the lateral difference in the input image(s) 604, of the input of the first neuron and the input of the second neuron is one pixel.

Neuron 602 may accept an input portion 606. The input portion 606 may include one or more pixels in the input image(s) 604. A size of the input portion 606 may correspond to a receptive field of the neuron 602. For example, if the receptive field of the neuron 602 is a 3×3 pixel area, the input portion 606 may include at least one pixel in a 3×3 pixel area of the input image(s) 604. The number of pixels in the receptive field that are included in the input portion 606 may depend on a dilation rate of the neuron 602. In various implementations, the neuron 602 may convolve (or cross-correlate) the input portion 606 with a filter 608. The filter may correspond to at least one parameter 610. In some examples, the parameter(s) 610 are set during training of a neural network including the block 600. The result of the convolution (or cross-correlation) performed by the neuron 602 may be output as an output portion 612. In some cases, the output portion 612 of the neuron 602 is further combined with outputs of other neurons in the block 600. The combination of the outputs may, in some cases, correspond to an output of the block 600.

Figure 7B:
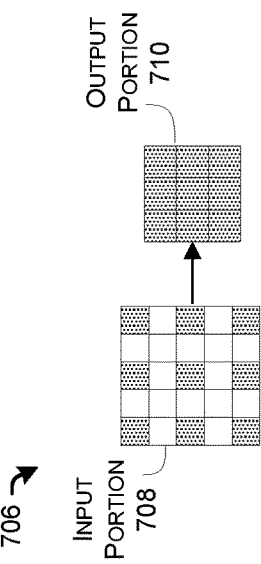
FIGS. 7A and 7B illustrate examples of dilation rates.
Figure 7A:
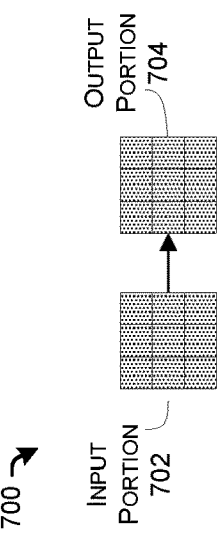

FIGS. 7A and 7B illustrate examples of dilation rates. In various implementations, the dilation rates illustrated in FIGS. 7A and 7B can be utilized by a neuron, such as the neuron 602 illustrated in FIG. 6. FIG. 7A illustrates a transformation 700 of a 3×3 pixel input portion 702 into a 3×3 pixel output portion 704. The dilation rate of the transformation 700 is equal to 1. The receptive field of a neuron utilizing the transformation 700 is a 3×3 pixel area. FIG. 7B illustrates a transformation 706 of a 3×3 pixel input portion 708 into a 3×3 pixel output portion 710. The dilation rate of the transformation 700 is equal to 2. The receptive field of a neuron utilizing the transformation 706 is a 5×5 pixel area.

Figure 8:
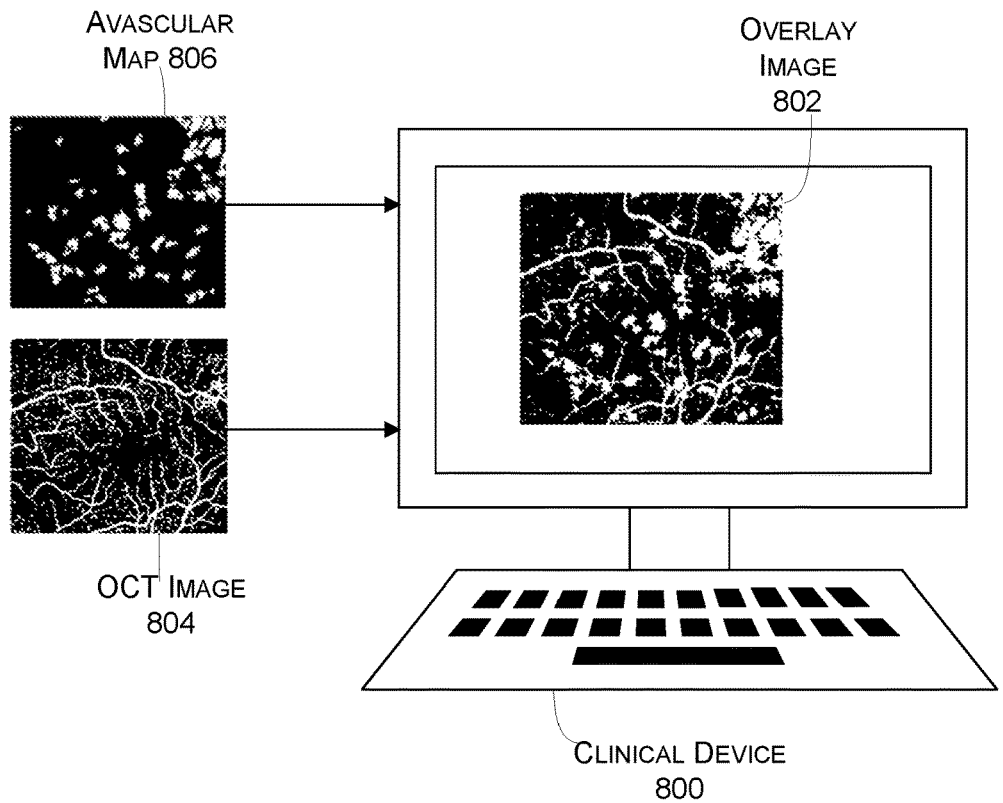
FIG. 8 illustrates an example of a clinical device configured to display an OCTA image overlaid with a corresponding avascular map.

FIG. 8 illustrates an example of a clinical device 800 configured to display an overlay image 802. In some cases, the clinical device 800 can correspond to the clinical device(s) 112 described above with reference to FIG. 1. Examples of the clinical device 800 can include a smart phone, a tablet computer, a personal computer, a holographic display, or the like.

The overlay image 802 may include an OCT image 804 overlaid with an avascular map 806. The OCT image 804 may be an OCTA image, in some cases. The avascular map 806, in certain examples, may be generated by a trained neural network (e.g., neural network 110) in response to receiving the OCT image 804 as an input. In certain examples, the OCT image 804 is generated by an OCT device (e.g., an OCTA device) that corresponds to the clinical device 800. In some cases, the OCT device is part of the clinical device 800. In certain implementations, the OCT device interfaces with the clinical device 800, such that the clinical device 800 can receive the OCT image 804 from the OCT device. In some cases, the OCT device can transmit the OCT image 804 to a prediction system (e.g., prediction system 102), which may, in turn, transmit the OCT image 804 to the clinical device 800 with the avascular map 806

In particular implementations, the avascular map 806 is a binary image. The overlay image 802 may include portions of the OCT image 804 that correspond to vascular areas of the avascular map 806. The overlay image 802 may further include portions of the avascular map 806 that correspond to avascular areas of the avascular map 806. Accordingly, the clinical device 800 can display the vascular regions of the OCT image 804 while emphasizing avascular regions depicted by the OCT image 804. A clinician may be able to diagnose complications of DR more efficiently using the overlay image 802 than by using the OCT image 804 alone.

Although not illustrated in FIG. 8, in some cases, the avascular map 806 can have three levels rather than just two. For instance, one level may correspond to vascular areas, one level may correspond to avascular areas, and one level may correspond to signal reduction areas. In these cases, the overlay image 802 may display areas of an underlying OCT image (e.g., an OCTA image) corresponding to the vascular areas, display a first color corresponding to the avascular areas, and display a second color corresponding to the signal reduction areas. The overlay image 400 described above with reference to FIG. 4 is an example of an overlay image illustrating signal reduction areas in addition to avascular areas.

Figure 9:
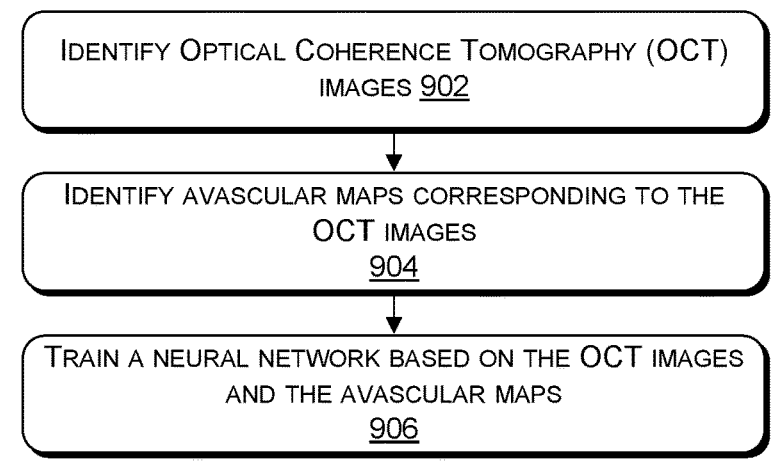
FIG. 9 illustrates an example of a process for training a neural network based on OCT images and avascular maps.

FIG. 9 illustrates an example of a process 900 for training a neural network based on OCT images and avascular maps. In some implementations, the process 900 can be performed by a prediction system (e.g., prediction system 102), a trainer (e.g., trainer 104), or a combination thereof.

At 902, OCT images may be identified. The OCT images may be captured from multiple eyes. According to particular examples, the OCT images may be captured from multiple eyes with different disease severities. In some cases, the OCT images may be captured by multiple imaging devices. In some cases, the OCT images can be derived from images captured by various imaging devices. The OCT images may include OCTA images, OCT reflectance images, OCT reflectance intensity maps, thickness images, B-scans, or a combination thereof.

At 904, avascular maps corresponding to the OCT images may be identified. In some cases, the avascular maps may be received from the same or different entity(s) that transmitted the OCT images. The avascular maps can be binary images identifying avascular areas of the OCT images. In some examples, the avascular maps further indicate signal reduction areas of the OCT images. For instance, each pixel in a given avascular map can have one of three levels—one level indicating that the pixel depicts an avascular area, one level indicating that the pixel depicts a signal reduction area, and one level indicating that the pixel does not depict an avascular area or a signal reduction area. In some cases, the avascular maps are generated by devices under direction of one or more experts, who may individually select pixels of the OCT images corresponding to avascular areas and/or signal reduction areas via one or more user interfaces. If multiple experts have different opinions about whether a particular pixel corresponds to an avascular area or a signal reduction area, the pixel is defined, in an avascular map, as whatever a majority of the experts believes the pixel to be.

At 906, a neural network may be trained based on the OCT images and the avascular maps. In various implementations, parameters in the neural network (e.g., scaling factors and/or values in filters utilized by neurons in the neural network) can be optimized in the neural network according to a loss function. By optimizing the parameters, the neural network can be trained to effectively transform the OCT images into the avascular maps with minimal loss. The trained neural network may then be used to transform new OCT images into new avascular maps.

Figure 10:
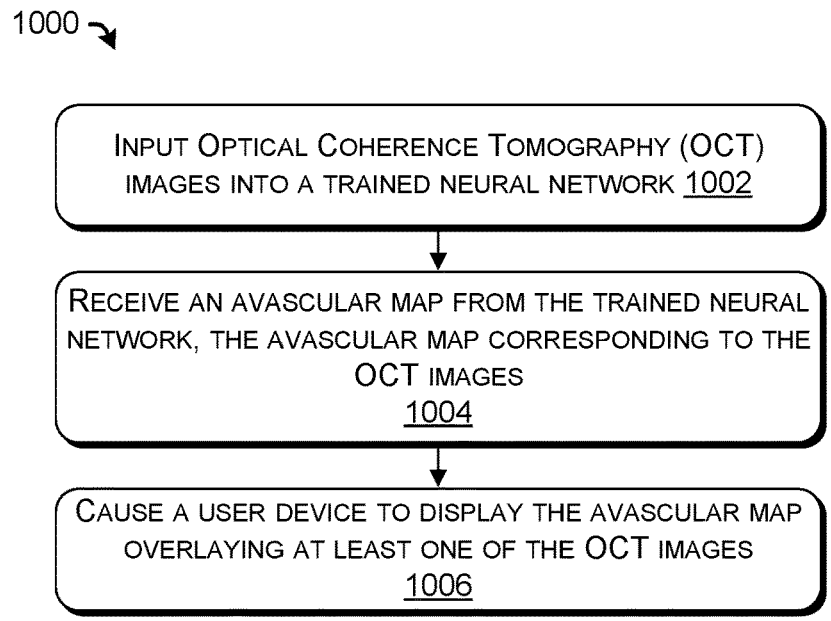
FIG. 10 illustrates an example of a process for utilizing a trained neural network by inputting an OCT image into the trained neural network.

FIG. 10 illustrates an example of a process 1000 for utilizing a trained neural network by inputting an OCT image into the trained neural network. In various implementations, the process 1000 can be performed by a prediction system (e.g., prediction system 102), a neural network (e.g., neural network 110), or a combination thereof.

At 1002, OCT images are input into a trained neural network. The OCT images may include at least one OCTA image, at least one OCT reflectance image, at least one thickness image, or a combination thereof. The OCT images may depict at least one portion of at least one eye of a patient. In some cases, the OCT image is received from a clinical device that has captured the OCT images or is in communication with a device that has captured the OCT images. The OCT images may be input into a first block of the trained neural network. In response, the neural network may process the OCT images.

At 1004, an avascular map may be received from the trained neural network. The avascular map may correspond to the OCT images input at 1002. In some cases, the avascular map can be a probability map, which indicates the probability that each pixel in at least one of the OCT images (e.g., an OCTA image) corresponds to an avascular area. In certain cases, the avascular map is a binary image that indicates whether each pixel has a greater than a threshold percentage probability (e.g., >50% probability) of depicting an avascular area. According to some implementations, the avascular map further indicates whether each pixel has greater than a threshold percentage probability (e.g., >50% probability) of depicting a signal reduction area. For instance, the avascular map may be an image in which each pixel has one of three levels—one level indicating that the pixel depicts an avascular area, one level indicating that the pixel depicts a signal reduction area, and one level indicating that the pixel does not depict an avascular area or a signal reduction area.

At 1006, the process 1000 may include causing a user device to display the avascular map overlaying at least one of the OCT images. In some implementations, the avascular map and/or the at least one OCT image may be transmitted to the user device. An instruction to output the avascular map overlaying the at least one OCT image may be transmitted to the user device. In some cases, the user device may be a clinical device that is operated by a clinician. Accordingly, the avascular map overlaying the at least one OCT image may assist the clinician with diagnosing complications of DR in the patient.

Figure 11:
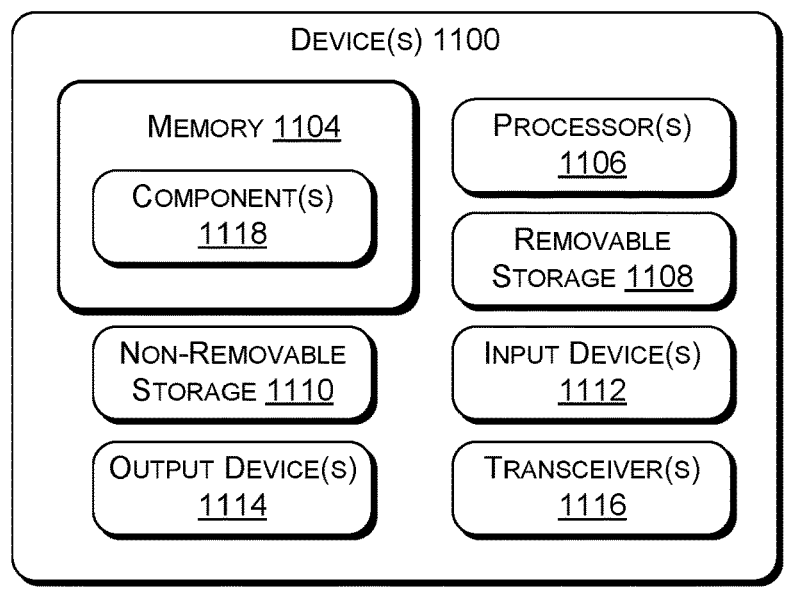
FIG. 11 illustrates an example system including at least one device for performing any of the functions described herein.

FIG. 11 illustrates at least one example device 1100 for performing any of the functions described herein. In some implementations, some or all of the functionality discussed in connection with FIGS. 1-10 can be implemented in the device(s) 1100. Further, the device(s) 1100 can be implemented as one or more server computers, a network element on a dedicated hardware, as a software instance running on a dedicated hardware, or as a virtualized function instantiated on an appropriate platform, such as a cloud infrastructure, and the like. It is to be understood in the context of this disclosure that the device(s) 1100 can be implemented as a single device or as a plurality of devices with components and data distributed among them.

As illustrated, the device(s) 1100 include a memory 1102. In various embodiments, the memory 1102 is volatile (such as RAM), non-volatile (such as ROM, flash memory, etc.) or some combination of the two. The memory 1102 may store, or otherwise include, various components 1104. In some cases, the components 1104 can include objects, modules, and/or instructions to perform various functions disclosed herein. The components 1104 can include methods, threads, processes, applications, or any other sort of executable instructions. The components 1104 can include files and databases. In some implementations, at least some of the components 1104 can be executed by processor(s) 1106 to perform operations. In some embodiments, the processor(s) 1106 includes a Central Processing Unit (CPU), a Graphics Processing Unit (GPU), or both CPU and GPU, or other processing unit or component known in the art. In some implementations, the components 1104 may include instructions for performing any of the functions described herein, such as functions of the prediction system 102, the trainer 104, the neural network 110, the clinical device(s) 112, or the like.

The device(s) 1100 can also include additional data storage devices (removable and/or non-removable) such as, for example, magnetic disks, optical disks, or tape. Such additional storage is illustrated in FIG. 1100 by removable storage 1108 and non-removable storage 1110. Tangible computer-readable media can include volatile and nonvolatile, removable and non-removable media implemented in any method or technology for storage of information, such as computer readable instructions, data structures, program modules, or other data. The memory 1102, removable storage 1108 and non-removable storage 1110 are all examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1100. Any such tangible computer-readable media can be part of the device(s) 1100. In some implementations, at least one of the memory 1102, the removable storage 1108, or the non-removable storage 1110 can include a neuromorphic memory device.

The device(s) 1100 also can include input device(s) 1112, such as a keypad, a cursor control, a touch-sensitive display, voice input device, etc., and output device(s) 1114 such as a display, speakers, printers, etc. In some implementations, the input device(s) 1112, in some cases, may include a device configured to capture OCT images, such as OCTA images. In certain examples, the output device(s) 1114 can include a display (e.g., a screen, a hologram display, etc.) that can display an OCT image (e.g., an OCTA image) overlaid with an avascular map, thereby indicating portions of the OCT image that correspond to areas of nonperfusion.

As illustrated in FIG. 11, the device(s) 1100 can also include one or more wired or wireless transceiver(s) 1116.

For example, the transceiver(s) 1116 can include a Network Interface Card (NIC), a network adapter, a Local Area Network (LAN) adapter, or a physical, virtual, or logical address to connect to the various base stations or networks contemplated herein, for example, or the various user devices and servers. The transceiver(s) 1116 can include any sort of wireless transceivers capable of engaging in wireless, Radio Frequency (RF) communication. The transceiver(s) 1116 can also include other wireless modems, such as a modem for engaging in Wi-Fi, WiMAX, Bluetooth, or infrared communication.

Figure 12C:
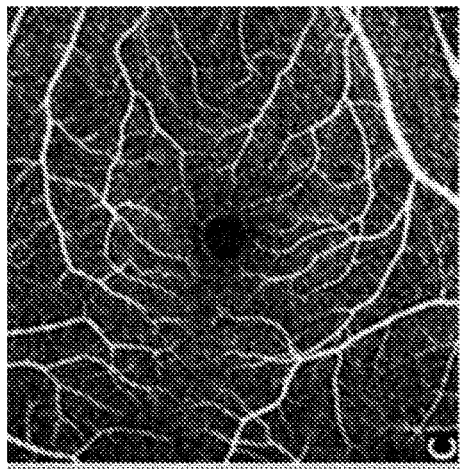
FIGS. 12A-12F illustrate examples of data acquisition for MEDnet-V2.
Figure 12F:
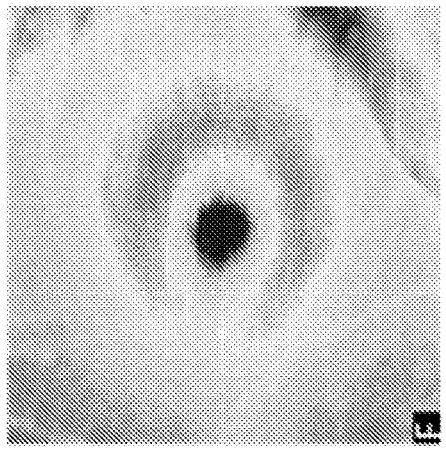
Figure 12B:
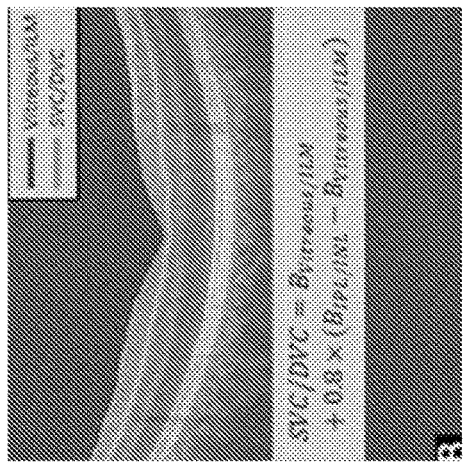
Figure 12E:
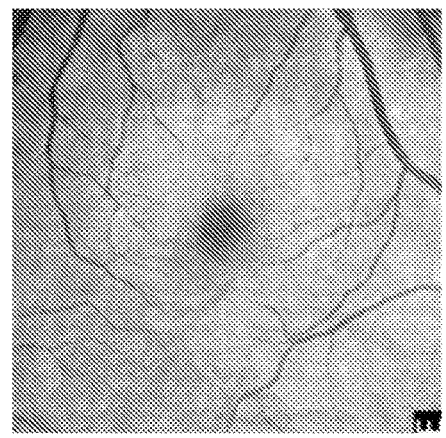
Figure 12A:
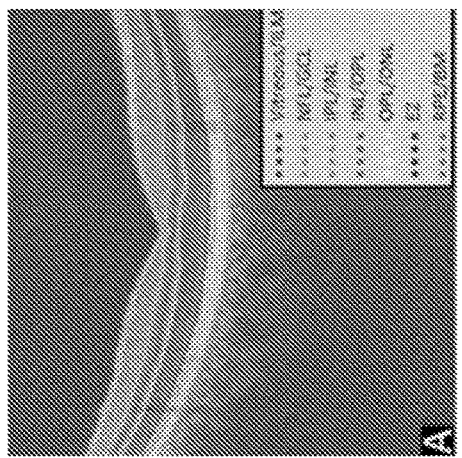
Figure 12D:

Example—Development and Validation of a Deep Learning Algorithm for Distinguishing Non-Perfusion Area from Signal Reduction Artifacts on OCT Angiography Capillary dropout in the retina is a biomarker for DR stage and progression. OCTA can be used to image NPA, but signal reduction artifacts caused by floater shadows, pupil vignetting, or defocus are significant obstacles to accurate quantification. In this example, a neural network (MEDnet-V2), is shown to accurately identify avascular regions and distinguish capillary dropout from signal reduction artifacts. MEDnet-V2 was tested and evaluated for distinguishing NPA from signal reduction artifacts in 6×6 mm² OCTA. The network achieves strong specificity and sensitivity for NPA detection across a range of DR FIGS. 12A-12F illustrate examples of data acquisition for MEDnet-V2. FIG. 12A illustrates example segmentation results of the retinal layer boundaries on a B-scan. FIG. 12B illustrates example definition of an SVC slab in the B-scan. FIG. 12C illustrates an example SVC angiogram produced by maximum projection of the OCTA data within the SVC slab. FIG. 12D illustrates example definition of the inner retina slab of the B-Scan. FIG. 12E illustrates an example reflectance image of the inner retina produced by mean projection of OCT data within the inner retina slab. FIG. 12F illustrates an example thickness map of the inner retina.

Various OCTA scans were acquired over a 6×6 mm² region using a 70-kHz OCT commercial AngioVue system (RTVue-XR; Optovue, Inc) centered at 840 mm with a full-width half maximum bandwidth of 45 nm. Two repeated B-scans were taken at each of 304 raster positions. Each B-scan included 304 A-lines. The OCTA data were calculated by using the Split-Spectrum Amplitude Decorrelation Angiography (SSADA) algorithm, which is described in Jia et al., Optics Express 20, 4710-25 (2012). Retinal layer boundaries (e.g., FIG. 12A)) were segmented by performing a Guided Bidirectional Graph Search (GB-GS) algorithm, which is described in Guo et al., Biomed. Optics Exp. 9, 4429 (2018). Angiograms of the SVC (e.g., FIGS. 12B-12C) and reflectance images of inner retina (e.g., FIGS. 12D-12E)] were generated by projecting OCTA/OCT data within the slab of interest. The thickness maps of the inner retina (FIG. 12F) were generated by projecting the distances between the inner limiting membrane (upper boundary) and the outer plexiform layer (lower boundary), excluding the contribution from retinal fluid.

Figure 13:
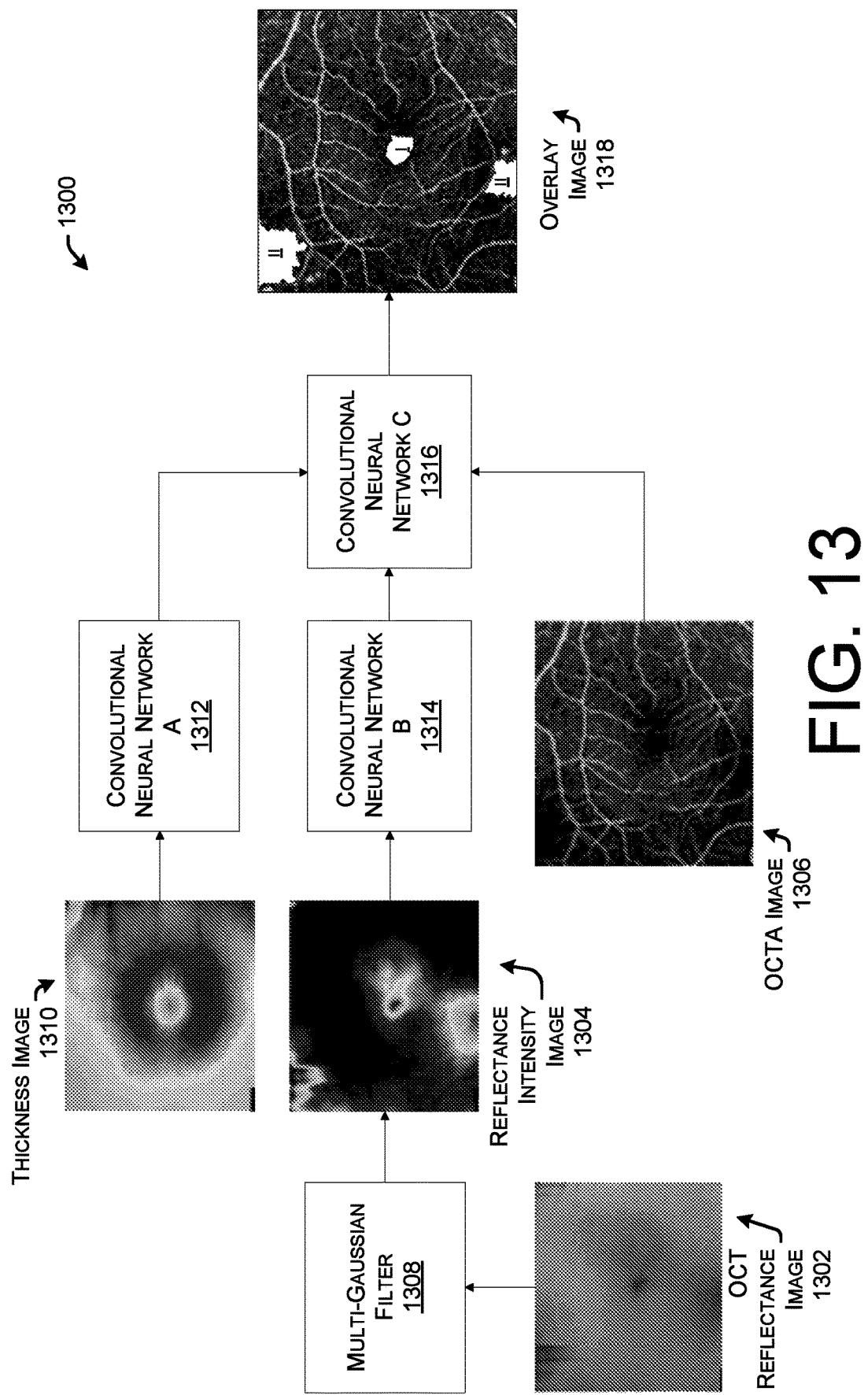
FIG. 13 illustrates an example of a brief network architecture of MEDnet-V2.

MEDne-V2 considers NPA segmentation as distinguishing three categories—perfusion, non-perfusion, and signal reduction. FIG. 13 illustrates an example of a brief network architecture 1300 of MEDnet-V2. OCT images including a OCT reflectance image 1302 of an inner retina, a Gaussian-filtered reflectance intensity map of the inner retina 1304, an inner retinal thickness map 1310, and an en face angiogram of the superficial vascular complex 1306 are utilized. CNN A 1312, CNN B 1314, and CNN C 1316 may have the same structure. A detection result in the form of an overlay image 1318 may indicate probability maps for perfusion loss (I) and signal reduction artifact (II).

Before feeding the en face OCT reflectance image 1302 into the network, a multi-Gaussian filter 1308 was applied to the OCT reflectance image 1302, in order to produce the reflectance intensity map 1304 and to remove artifacts (e.g. due to large vessels) and noise. The multi-Gaussian filter is represented by Equation 4:

$$M = \varphi\left(\frac{1}{N}\sum_{i=1}^{N}G(h, \sigma_i) * \left(I - \overline{I} + \frac{1}{N}\right)\right) \quad (4)$$

wherein $\varphi(\bullet)$ is a rectifier function that sets a matrix element value to 1 if the element value is greater than 1. N is the number of Gaussian filters. $G(h,\sigma_i)$ is the Gaussian filter with size of h×h (h=9) and standard deviation of $\sigma_i$ ($\sigma$=[9, 15,21]). * is the convolution operator, I is the matrix of the image, and $\overline{I}$ is the mean value of image.

In the reflectance intensity map 1304, both the fovea and shadow-affected areas exhibited low reflectance. To distinguish the fovea and shadow-affected areas, the thickness map of the inner retina 1310, which shows low values around fovea area, was fed into a subnetwork to remove its impact on the detection of signal reduction artifacts. After passing through the two convolutional neural networks 1312 and 1314, the features from the reflectance intensity map 1304 and the inner retinal thickness map 1310 were added together (i.e., a pixel-wise addition of the two maps). Then, the en face angiogram of the SVC 1306 was concatenated with the features from the previous networks 1312 and 1314 and fed to the last neural network 1316. The last neural network 1316 outputs an avascular map, which is used to generate the overlay image 1318 based on the OCTA image 1306.

Figure 14A:
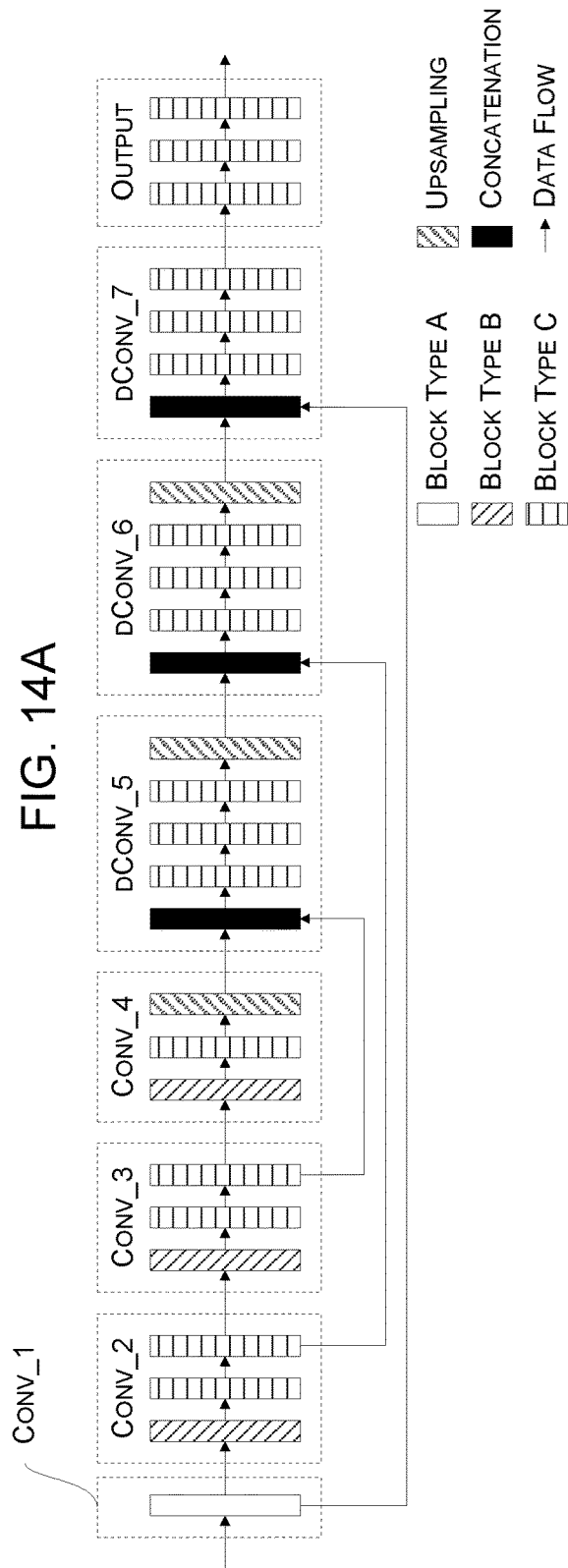
FIG. 14A illustrates an example network architecture of one subnetwork of MEDnet-V2.
Figure 14D:
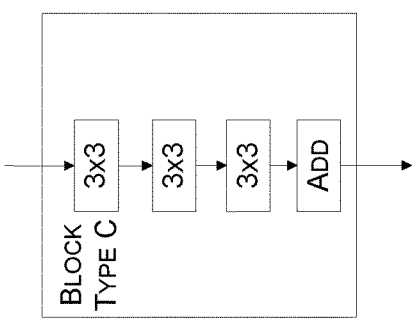
FIGS. 14C and 14D illustrate examples of residual blocks from ResNet, which can be used in the subnetwork of FIG. 14A.
Figure 14E:
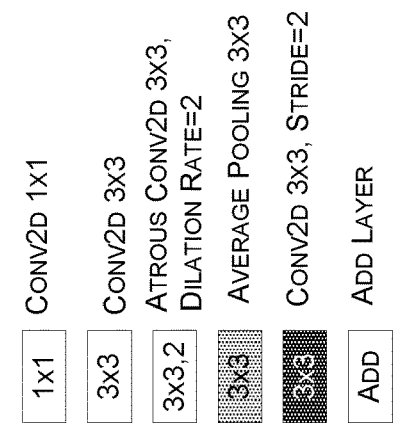
FIG. 14E identifies some of the blocks and/or layers that are included in FIGS. 14B-14D.
Figure 14C:
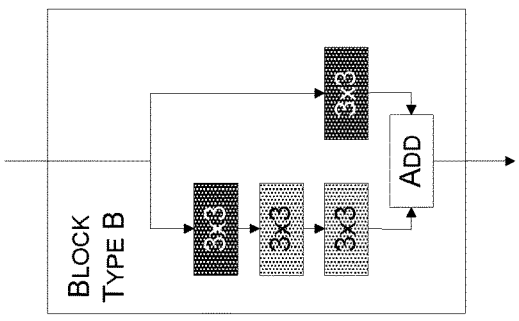
Figure 14B:
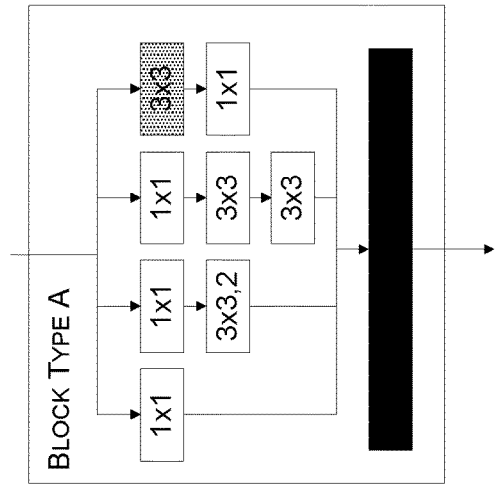
FIG. 14B illustrates an example of a multi-scale convolutional block.

FIG. 14A illustrates an example network architecture of one subnetwork (e.g., one of (1312 to 1316 of MEDnet-V2. FIG. 14B illustrates an example of a multi-scale convolutional block (block type A). FIGS. 14C and 14D illustrate examples of residual blocks (block types B and C) from ResNet, which can be used in the subnetwork of FIG. 14A. FIG. 14E identifies some of the blocks and/or layers that included in FIGS. 14B-14D.

As illustrated in FIG. 14A, MEDnet-V2 includes three sub convolution networks (also referred to as "subnetworks"), each with identical structure. The sub convolution network uses a U-net-like architecture. FIG. 14B illustrates a version of the modified multi-scale module. In each encoder and decoder block, plain connection blocks were replaced with residual blocks (FIGS. 14C and 14D) from ResNet, which are described, e.g., in He et al., Frontiers in Psychology 4, 770-78 (2015). After each convolution operation, a batch normalization operation was introduced to accelerate the training phase and reduce overfilling.

As illustrated in FIG. 14A, the network can be divided into two parts, encoder and decoder. In the encoder section, a multi-scale block (FIG. 14B) was employed to extract multi-scale features from input images. The multi-scale block includes four blocks including one or more convolution layers arranged in parallel. The outputs of the blocks were concatenated across the depth dimension into a single tensor before being fed to the next layer. After that, each "Cony block" includes multiple convolution layers, each of which includes a batch normalization stage, an activation stage (using a rectified linear unit (ReLU)) and a max pooling operation. "Conv2d 1×1" convolves a 1×1 pixel filter with a stride=1, "Conv2d 3×3" convolves a 3×3 pixel filter with a stride=1, "Atrous Conv2d 3×3, dilation rate=2" convolves a 3×3 pixel filter with a dilation rate=2 and a stride=1, and "Conv2d 3×3, stride=2" convolves a 3×3 pixel filter with a stride=2. The batch normalization was applied to accelerate deep network training and reduce overfilling. The role of the convolution blocks (Conv_1, Conv_2, Conv_3, and Conv_4) was to encode the image whereas dConv_5, dConv_6 and dConv_7 made up the decoder. The decoder blocks received the outputs of encoder blocks through across-layer connections that allowed the resolution of the output to be preserved and stabilized the training phase. For instance, the output of Conv_1 is input into dConv_7, the output of Conv_2 is input into dConv_6, and the output of Conv_3 is input into dConv_5. The across-layer connections are also used in U-Net-based networks. See generally Ronneberger et al., MEDICAL IMAGE COMPUTING AND COMPUTER-ASSISTED INTERVENTION—MICCAI 2015, Navab, et al., eds. (2015), pp. 234-41 & Roy et al., BIOMED. OPT. EXPRESS 8(8), 3627-42 (2017). A softmax activation function was used in the output block for pixel-wise classification. Thus, the output block produces a binary image.

Figure 15D:
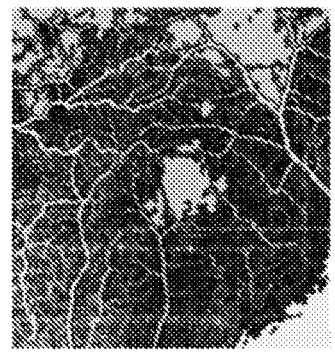
FIGS. 15A to 15D illustrates an example of a representative input data set.
Figure 15C:
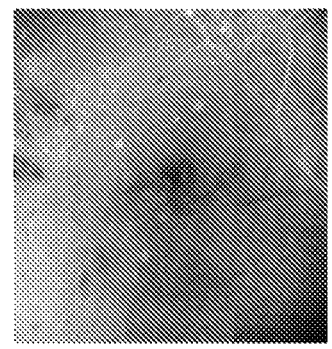
Figure 15B:
Figure 15A:
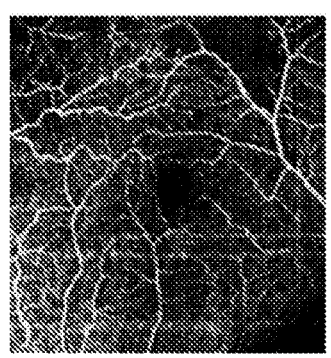

FIGS. 15A-15D illustrate an example of a representative input data set. FIG. 15A illustrates an en face angiogram of a superficial vascular complex from a patient with diabetic retinopathy. FIG. 15B illustrates an inner retinal thickness map of the patient. FIG. 15C illustrates a reflectance image acquired by projecting the reflectance OCT data within the inner retina. FIG. 15D illustrates an example of a ground truth map of the non-perfusion area (green) and signal reduction artifact (yellow) overlaid on the superficial vascular complex angiogram.

The input data set included en face angiograms of the SVC (e.g., FIG. 15A), the corresponding inner retinal thickness maps (FIG. 15B), the corresponding inner retina OCT reflectance images (FIG. 15C), and the corresponding manually delineated NPA and the regions affected by signal reduction artifact (FIG. 15D).

The data set was collected from 180 participants in a clinical DR study (76 healthy controls, 34 participants with diabetes without retinopathy, 31 participants with mild or moderate non-proliferative DR (NPDR) and 39 participants with severe DR. Two repeat volume scans were acquired from the same eye of each participant. OCTA scans were also acquired from 12 healthy volunteers, and 6 repeat volume scans (one reference scan, two scans with manufactured shadow, and three defocused scans with different diopters) were acquired from each volunteer (Table 1). To increase the number of training samples, several data augmentation operations, including addition of Gaussian noise (mean=0, sigma=0.5), salt and pepper (salt=0.001, pepper=0.001), horizontal flipping, and vertical flipping, were applied.

TABLE 1

Data set used in MedNet-V2

| | Clinical DR study | | | Manufactured signal strength reduction group | |
|---|---|---|---|---|---|
| | Severe DR | Mild to moderate NPDR | Diabetes without retinopathy | Healthy control | Healthy control |
| Eyes/scans | 39/78 | 31/62 | 34/68 | 76/152 | 12/72 |

In a healthy eye, NPA is concentrated in the macular area and accounts for a very small proportion of an overall en face angiogram. Even in an eye with DR, NPA rarely achieves similar proportions as healthy (blood flow perfused) areas. Moreover, signal strength reduction can affect en face angiograms at any location. These issues can cause a serious category imbalance problem in this segmentation task. To address this, a novel weighted Jaccard coefficient loss function (Equation 5) was utilized. The following Equation 5 is an example loss function that imposes different weights to each category (i.e., vascular/perfusion area, avascular/nonperfusion area, and signal reduction area) to adjust the category balance:

$$L = \sum_{i=1}^{N} J_i \times w_i, \quad \sum_i w_i = 1, \tag{5}$$

$$J = \left(1 - \frac{\sum_x y(x) \times \hat{y}(x) + \alpha}{\sum_x (y(x) + \hat{y}(x)) - \sum_x y(x) \times \hat{y}(x) + \alpha}\right) \times \alpha.$$

wherein N is category index, and $w_i$ is the weight of i-th category associated with Jaccard coefficient $J_i$. In this task, we set the three categories (healthy area, NPA, and signal reduction artifacts) with weights as w=(0.25, 0.5, 0.25). x denotes the position of each pixel, y(x) is ground truth, $\hat{y}(x)$ is the output of the network, and a is a smoothing factor set to 100.

The Adam algorithm (described, e.g., in Kingma et al., AIP CONFERENCE PROCEEDINGS 1631, 58-62 (2014)), a stochastic gradient-based optimizer, was utilized with an initial learning rate 0.001 to train the networks by minimizing the weighted Jaccard coefficient loss function. An additional global learning decay strategy was employed to reduce the learning rate during training. In this learning rate decay strategy, the learning rate was reduced until the loss did not decrease after 10 epochs. This decay strategy will stop when the learning rate is lower than $1 \times 10^{-6}$. The training process will also stop when both the learning rate and loss stop declining. MEDnet-V2 was implemented in Python 3.6 with Keras (Tensorflow-backend) on a PC with an Intel i7 CPU, NVidia GeForce GTX 1080Ti graphics card, and 32G RAM.

Six-fold cross validation was applied to evaluate the performance of MEDnet-V2 on the data set. The data set was split into six subsets. Six networks were trained on five of these six subsets alternately and validated on the remaining one. The performance of the network might be affected by several factors, principally the severity of the disease and low OCT Signal Strength Index (SSI). The test set into two groups: a group with different disease severity and a group with different SSI. For each group, scans were divided into 4 different sub-groups according to a gradient of disease severity or SSI. 4 measures (accuracy, specificity, sensitivity, and dice coefficient) and NPA of each sub-groups (Table 2) were calculated. The following Equations 6 illustrate example calculations for the 4 measures:

$$\text{Accuracy} = \frac{TP + TN}{TP + FP + TN + FN} \tag{6}$$

$$\text{Specificity} = \frac{TN}{TN + FP}$$

$$\text{Sensitivity} = \frac{TP}{TP + FN}$$

$$Dice = \frac{2 \times TP}{2 \times TP + FP + FN}$$

wherein TP is true positives (correctly predicted NPA pixels), TN is true negatives (healthy area and signal reduction artifacts were considered as negatives), FP is false positives (healthy or signal reduced area segmented as NPA), and FN is false negatives (NPA segmented as either healthy or artifact). In our analysis, the specificity approached unity across disease state and SSI, indicating nearly perfect segmentation of healthy tissue. Sensitivity and dice coefficient deteriorated as the severity of disease increasing, because of the cumulative error will increase with the increase of complexity and NPA. In the SSI group, sensitivity and dice coefficient didn't show obvious decline as SSI decreased, which indicates that the network was robust to low-quality images and avoided introducing an artificial trend into the NPA measurements.

TABLE 2

Agreement (in pixels) between automated detection and manual delineation of non-perfusion area (mean ± standard deviation)

| | | Accuracy | Specificity | Sensitivity | Dice coefficient | Detected NPA (mm$^2$) |
|---|---|---|---|---|---|---|
| Disease severity | Control | 1.00 ± 0.00 | 1.00 ± 0.00 | 0.92 ± 0.07 | 0.93 ± 0.04 | 0.27 ± 0.11 |
| | Diabetes without retinopathy | 0.99 ± 0.00 | 0.99 ± 0.01 | 0.89 ± 0.11 | 0.88 ± 0.08 | 0.56 ± 0.13 |
| | Mild to moderate DR | 0.99 ± 0.01 | 0.99 ± 0.00 | 0.83 ± 0.13 | 0.87 ± 0.10 | 1.70 ± 0.67 |
| | Severe DR | 0.95 ± 0.03 | 0.98 ± 0.01 | 0.78 ± 0.14 | 0.82 ± 0.08 | 4.87 ± 1.72 |
| SSI (In healthy controls) | >71 | 1.00 ± 0.00 | 1.00 ± 0.00 | 0.93 ± 0.07 | 0.90 ± 0.07 | 0.31 ± 0.15 |
| | 66-71 | 1.00 ± 0.00 | 1.00 ± 0.00 | 0.95 ± 0.01 | 0.88 ± 0.08 | 0.25 ± 0.13 |
| | 61-65 | 0.98 ± 0.00 | 0.99 ± 0.00 | 0.95 ± 0.05 | 0.90 ± 0.05 | 0.32 ± 0.18 |
| | 50-60 | 0.99 ± 0.00 | 1.00 ± 0.00 | 0.96 ± 0.03 | 0.87 ± 0.07 | 0.38 ± 0.16 |

Signal reduction artifacts originate in a variety of ways. As a supplement to the data set, several typical signal reduction artifacts were simulated on healthy controls.

Figure 16:
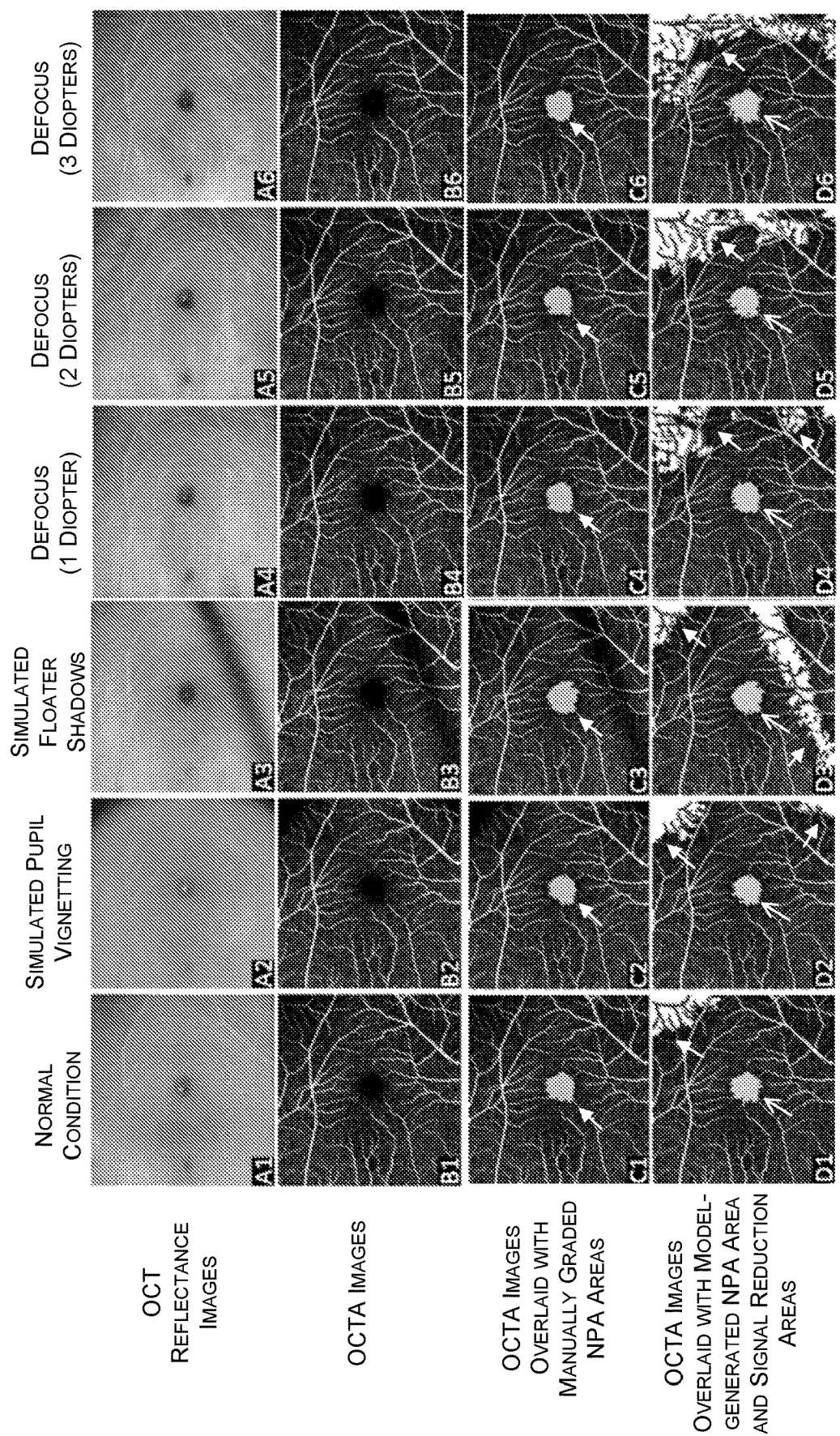
FIG. 16 illustrates example results of simulated signal reduction artifacts on healthy controls by MEDnet-V2.

FIG. 16 illustrates example results of simulated signal reduction artifacts on healthy controls by MEDnet-V2. Portions (A1)-(D1) illustrate reference scans under normal conditions. Portions (A2)-(D2) illustrate scans with simulated pupil vignetting. Portions (A3)-(D3) illustrate scans with simulated floater shadows. Portions (A4)-(D4) illustrate scans with 1 diopter defocus. Portions (A5)-(D5) illustrate scans with 2 diopters defocus. Portions (A6)-(D6) illustrate scans with 3 diopters defocus. In FIG. 16, first row (A) illustrates the en face images of inner retinal reflectance, second row (B) illustrates the corresponding en face angiograms of superficial vascular complex, third row (C) illustrates the ground truth of the non-perfusion areas generated manually by an expert grader, overlaid on the en face angiograms, and the last row (D) illustrated the predicted results of non-perfusion areas (shapes indicated by open arrows) and signal reduction artifacts (shapes indicated by solid arrows) by MEDnet-V2 overlaid on the en face angiograms.

For each healthy control, a scan under normal conditions was acquired as a reference (e.g., (A1)-(D1) of FIG. 6). Then, we acquired a scan with simulated pupil vignetting (e.g., (A2)-(D2) of FIG. 16), a scan with simulated floater shadows (e.g., (A3)-(D3) of FIG. 16), and three defocus scans with diopters ranging from 1 to 3 (e.g., (A4)-(D4), (A5)-(D5), and (A6)-(D6) of FIG. 16) to simulate clinical signal reduction artifacts. The results of MEDnet-V2 shows that the signal reduction artifacts can be well distinguished from NPA (e.g., (D1)-(D6) of FIG. 16).

Figure 17:
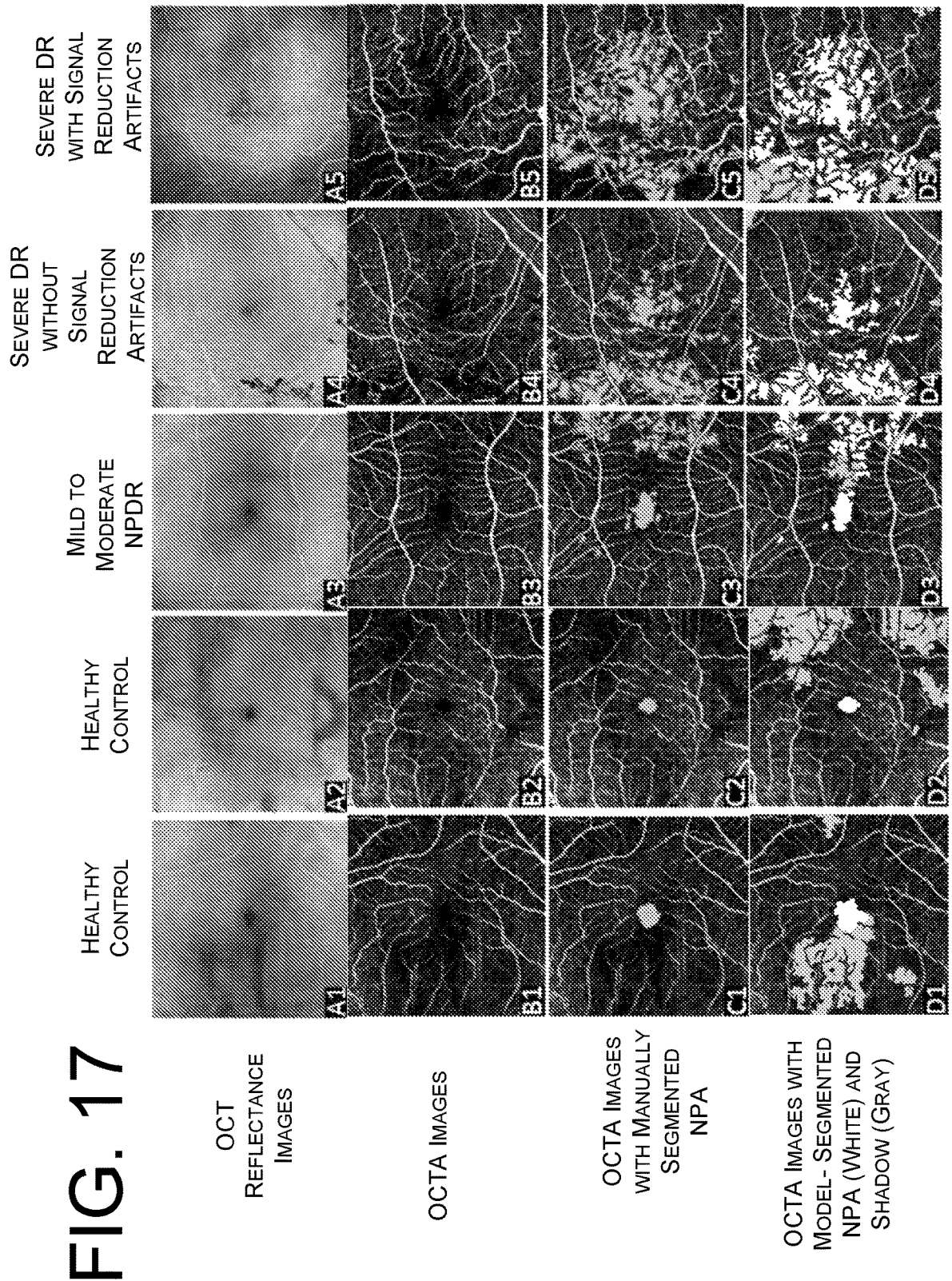
FIG. 17 illustrates example results of non-perfusion area detection on clinical cases using MEDnet-V2.

FIG. 17 illustrates example results of non-perfusion area detection on clinical cases using MEDnet-V2. In FIG. 17, (A1)-(D1) illustrate signal reduction artifacts connected to the macular area on a healthy control; (A2)-(D2) illustrate a healthy case with signal reduction artifacts caused by floater shadows and vignetting; (A3)-(D3) illustrate a severe DR case with no signal reduction artifacts; (A4)-(D4) illustrate a mild to moderate DR case with signal reduction artifacts; and (A5)-(D5) illustrate a severe DR case with strong signal reduction artifacts. A first row (A) illustrates the inner retinal reflectance en face images. A second row (B) illustrates the en face superficial vascular complex angiograms. A third row (C) illustrates the ground truth of the non-perfusion areas generated manually by an expert grader, overlaid on the en face angiograms. A last row (D) illustrates the predicted results of non-perfusion areas (white) and signal reduction artifacts (gray) by MEDnet-V2 overlaid on the en face angiograms.

In clinical cases, the signal reduction artifacts are considerably more complex than simulated ones. Shadows on en face angiograms may connect to the center of the macula (e.g., (A1)-(D1) of FIG. 17), and several kinds of signal reduction artifacts can overlap ((e.g., (A2)-(D2) of FIG. 17). Since NPA and signal reduction artifacts can occur anywhere in our OCTA scans on eyes with DR, the two may co-occur (e.g., (D3)-(D5) of FIG. 17). When the signal reduction artifacts combined with NPA (e.g., (D4)-(D5) of FIG. 17), MEDnet-V2 can still produce an accurate prediction result.

The repeatability was calculated using the pooled standard deviation (Equation 7, below) and coefficient of variation (Equation 8, below) in total 44 healthy eyes with two intra-visit repeated scans (Table 3).

$$P = \sqrt{\frac{1}{N}\sum_{i=1}^{N} s_i^2} \qquad (7)$$

-continued $$C = \frac{P}{\frac{1}{N}\sum_{i=1}^{N}\mu_i} \quad (8)$$

wherein P is the pooled standard deviation, C is the coefficient of variation, N is the number of eyes, s is the NPA standard deviation of two repeat scans from the same eye, and µ is the mean NPA of two repeat scans from the same eye. In the DR group, the mean and standard deviation of NPA is larger than that in healthy controls, as we expect given the nature of the pathology. Pooled standard deviation and coefficient of variation also deteriorated within DR group, because the cumulative error of detection of NPA will increase as NPA grows.

TABLE 3

Repeatability of MEDnet-V2 on NPA detection

| | Healthy (N = 44) | Diabetic retinopathy (N = 40) |
|---|---|---|
| NPA (mm$^2$, mean ± std.) | 0.31 ± 0.15 | 2.71 ± 2.34 |
| Pool std. (mm$^2$) | 0.03 | 0.41 |
| Coefficient of variation | 0.09 | 0.13 |

Defocus can cause signal loss, which may affect the detection of NPA in en face angiogram. To test the robustness of MEDnet-V2 to defocus, MEDnet-V2 was applied to 5 eyes.

Figure 18:
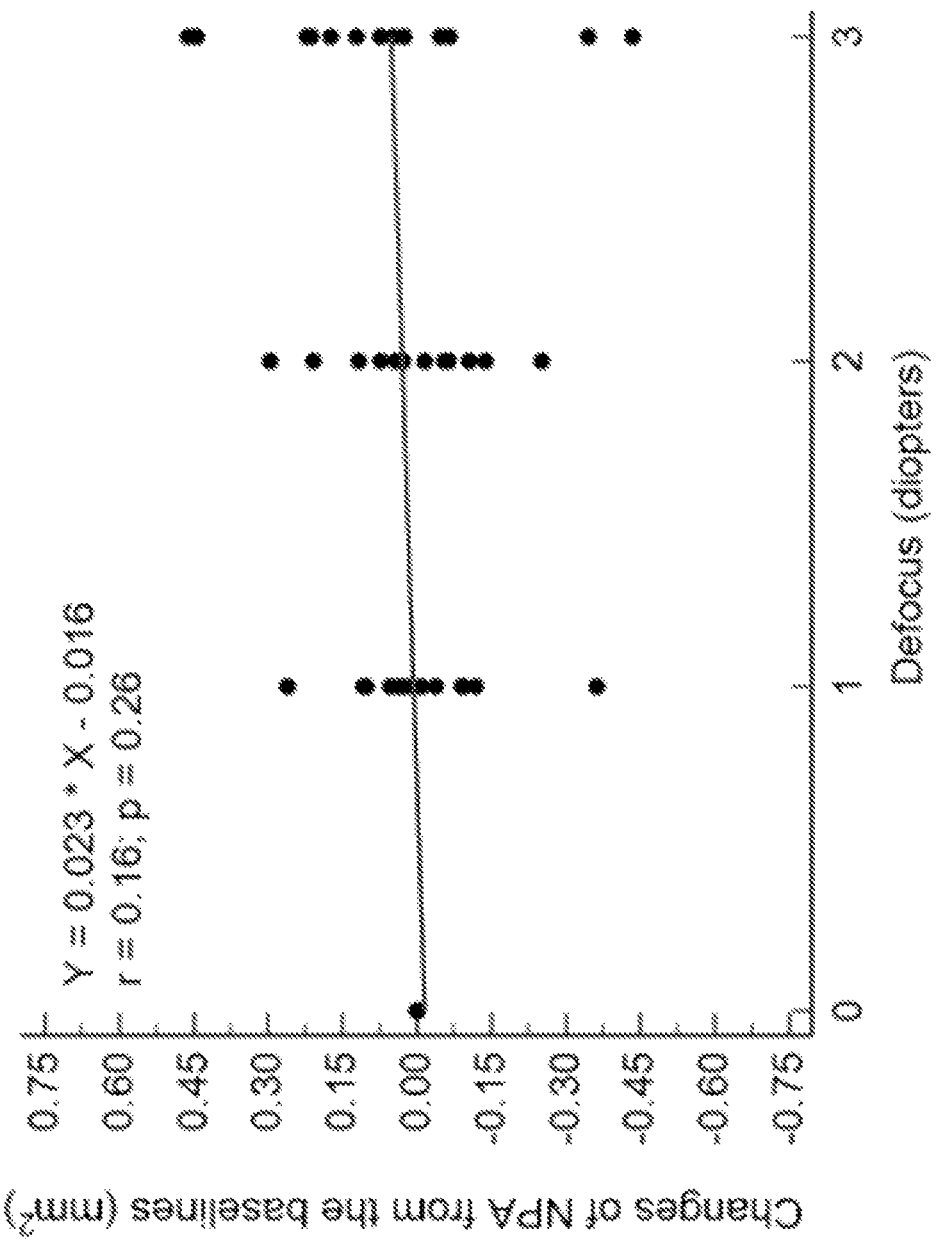
FIG. 18 illustrates a relationship of defocus and NPA detection results by MEDnet-V2.

FIG. 18 illustrates a relationship of defocus and NPA detection results by MEDnet-V2. Each eye was scanned four times with diopter levels from 0 to 3. As illustrated in FIG. 18, the low coefficient of determination (r=0.13) and a low significance level (p=0.345) indicates that the NPA detection results by MEDnet-V2 are not affected by defocus.

MEDnet-V2 is a refined method for NPA detection. NPA is a key biomarker for DR, but its utility in OCTA imaging has heretofore been seriously hindered by the inability of automated algorithms to correctly manage complications introduced by artifacts. OCTA is an extremely powerful technology in terms of the vascular detail it can capture (i.e., it obtains high resolution, volumetric data), but even in the best circumstances it is prone to imaging artifacts. See Spaide et al., PROGRESS IN RETINAL AND EYE RESEARCH 64, 1-55 (2018). This drawback is exacerbated for scans of DR eyes, which are often rich in complications but poor in quality. NPA then, though an excellent indicator of DR progression, will ultimately remain clinically under-utilized until algorithms can distinguish true NPA can be correctly distinguished from dropout due to shadowing artifact. The problem is relatively intractable for traditional image analysis techniques. Previously published results that relied on such approaches have then either ignored complications from shadowing artifacts (see, e.g., Schottenhamml et al., RETINA 36, S93 (2016); Agemy et al., RETINA 35, 2353-2363 (2015); & Nesper et al., INVESTIGATIVE OPHTHALMOLOGY & VISUAL SCIENCE 58, B10307-610315 (2017)) or required manual correction (see, e.g., Alibhai et al., RETINA (Philadelphia, Pa.) (2018)). Similarly, MEDnet-V1, which was also based on a deep learning approach, failed to distinguish shadowing artifact from true NPA. MEDnet-V1 is described, for instance, in Guo et al., BIOMED. OPT. EXPRESS 9(11), 5147-58 (2018).

MEDnet-V2 is a significant improvement over MEDnet-V1, principally because MEDnet-V2 can accurately distinguish between true NPA and signal reducing artifacts without appealing to user input. As a result, MEDnet-V2 provides more accurate and precise measurements of NPA. Gains in precision are of course always useful, but discriminating signal reducing artifacts from NPA enables the use of data from lower quality scans to generate accurate and precise measurements of NPA. MEDnet-V2 provides the ability to utilize more OCTA data, which can be used to more accurately quantify diseases, such as retinal ischemia.

MEDnet-V2 achieves these results through several architectural decisions. MEDnet-V2 has a U-net-like architecture that enables obtaining a stable training process while achieving high resolution in the output results. MEDnet-V1 showed excellent feature extraction ability. As the size of the network was expanded by embedding new structures from state-of-the-art networks, MEDnet-V2 correspondingly acquired a stronger ability to extract an expanded cohort of features. As shown in this example, MEDnet-V2 gives excellent performance (dice coefficient 0.87) on scans of different disease severity and defocus.

MEDnet-V2 provides a deep learning-based solution to address the problem of signal reduction artifacts in the detection and quantification of capillary dropout in the retina using OCTA. The network contains three kinds of input images, and outputs a non-perfusion area and signal reduction artifacts distribution map. Features of signal reduction artifacts and non-perfusion area were extracted separately before being fused together, which is the key to this network's favorable performance. The commendable performance on HD scans also indicates that MEDnet-V2 should have good adaptability to evolving OCTA imaging requirements.

Example Clauses

The following clauses represent various examples of implementations described herein. However, implementations are not limited to any of the following clauses. Various implementations of the present disclosure can include any combination of features recited in the example clauses.

1. A method of training a neural network to output an avascular map in response to receiving an OCTA image.
2. The method of clause 1 including training the neural network using training images of retinas and training avascular maps corresponding to the training images.
3. The method of clause 2, wherein the training images include training OCTA images and training reflectance intensity maps.
4. The method of clause 2 or 3, wherein the training images include inner retinal thickness maps of the retinas.
5. The method of clause 4, further including generating the inner retinal thickness maps by applying a Multi-Gaussian filter on cross-sectional images of the retinas.
6. The method of any of clauses 1 to 5, wherein the avascular map indicates an avascular region of the OCTA image and a signal reduction area of the OCTA image.
7. The method of clause 6, wherein the avascular map further indicates a vascular region of the OCTA image.
8. The method of any one of clauses 1 to 7, wherein the neural network includes multiple subnetworks.
9. The method of clause 8, wherein each of the subnetworks includes: a multi-scale block including multiple convolution blocks that apply different dilation rates and a merge block that concatenates outputs from the multiple convolution blocks.

10. A method, including: identifying a plurality of first images of a plurality of first retinas, the plurality of first images including thickness images of the first retinas, reflectance intensity maps of the first retinas, and OCTA images of the first retinas; identifying a plurality of first avascular maps corresponding to the plurality of first images; and training a neural network based on the plurality of first images and the plurality of first avascular maps.

11. The method of clause 10, further including: generating the reflectance intensity maps by filtering OCT reflectance images depicting the first retinas with a multi-Gaussian filter.

12. The method of clause 10 or 11, further including: generating the thickness images from cross-sectional images depicting the first retinas.

13. The method of any one of clauses 10 to 12, wherein at least one of the first avascular maps includes first and second levels, the first level indicating a vascular area in a particular one of the first images and the second level indicating an avascular area in the particular first images.

14. The method of clause 13, wherein the at least one of the first avascular maps further includes a third level, the third level indicating a signal reduction area in the particular first image.

15. The method of any of clauses 10 to 14, wherein the neural network includes multiple subnetworks.

16. The method of clause 15, wherein a first subnetwork among the multiple subnetworks receives the inner retinal thickness maps and outputs a first output, wherein a second subnetwork among the multiple subnetworks receives the reflectance intensity maps and outputs a second output, and wherein a third subnetwork among the multiple subnetworks receives the first output, the second output, and the OCTA images, and outputs a plurality of second avascular maps.

17. The method of clause 16, wherein the multiple subnetworks include a plurality of convolution blocks, and wherein training the neural network includes optimizing parameters associated with the convolution blocks to minimize a loss between the first avascular maps and the second avascular maps.

18. The method of clause 17, wherein the loss is below a predetermined threshold.

19. The method of any one of clauses 15 to 18, wherein at least one of the subnetworks includes a multi-scale block, the multi-scale block including: multiple first convolution blocks arranged in parallel, the first convolution blocks corresponding to different dilation rates; and a merge layer configured to combine the outputs from the first convolution blocks.

20. The method of any of clauses 15 to 19, wherein at least one of the subnetworks includes multiple second convolution blocks arranged in series.

21. The method of clause 20, wherein at least one of the second convolution blocks includes at least one convolution layer.

22. The method of clause 21, wherein the at least one of the second convolution blocks further includes an upsampling layer and a concatenation layer.

23. The method of any one of clauses 20 to 22, wherein at least one of the second convolution blocks includes: multiple first convolution layers arranged in series; a second convolution layer arranged in parallel with the multiple first convolution layers; and a merge layer combining an output from the multiple first convolution layers and an output from the second convolution layer.

24. The method of any one of clauses 20 to 23, wherein at least one of the second convolution blocks includes: multiple first convolution layers arranged in series; and a merge layer combining an output from the multiple first convolution layers and an input to the multiple first convolution layers.

25. The method of any one of clauses 10 to 24, further including: inputting second images into the neural network, the second images including a thickness image of a second retina, a reflectance intensity map of the second retina, and an OCTA image of the second retina; and receiving a second avascular map from the neural network, the second avascular map corresponding to the second images.

26. The method of any one of clauses 1-25, which is a method of training a neural network.

27. A method including generating an avascular map by inputting an OCTA image into a neural network.

28. The method of clause 27 including training the neural network using training images of retinas and training avascular maps corresponding to the training images.

29. The method of clause 27 or 28 wherein generating the avascular map includes inputting a reflectance intensity map into the neural network.

30. The method of any one of clauses 27 to 29 wherein generating the avascular map includes inputting an inner retinal thickness map into the neural network.

31. The method of clause 30, further including generating the inner retinal thickness map by applying a Multi-Gaussian filter on a cross-sectional image of a retina.

32. The method of any one of clauses 27 to 31, wherein the avascular map indicates an avascular region of the OCTA image and a signal reduction area of the OCTA image.

33. The method of clause 32, wherein the avascular map further indicates a vascular region of the OCTA image.

34. The method of any one of clauses 27 to 33, wherein the neural network includes multiple subnetworks.

35. The method of clause 34, wherein each of the subnetworks includes: a multi-scale block including multiple convolution blocks that apply different dilation rates and a merge block that concatenates outputs from the multiple convolution blocks.

36. A method, including: inputting first images into a trained neural network, the first images including a thickness image of a first retina, a reflectance intensity map of the first retina, and an OCTA image of the first retina; and receiving a first avascular map from the trained neural network, the first avascular map corresponding to the first images.

37. The method of clause 36, wherein the trained neural network was trained based on a plurality of second images of a plurality of second retinas and a plurality of second avascular maps corresponding to the plurality of second images.

38. The method of clause 37, wherein the plurality of second images includes thickness images of the second retinas, reflectance intensity maps of the second retinas, and OCTA images of the second retinas.

39. The method of any one of clauses 36 to 38, wherein receiving the first avascular map includes: generating, using the trained neural network, the first avascular map.

40. The method of any of clauses 36 to 39, wherein the first avascular map includes first and second levels, the first level indicating a vascular of the OCTA image and the second level indicating an avascular area of the OCTA image.
41. The method of clause 40, wherein the first avascular map further includes a third level, the third level indicating a signal reduction area of the OCTA image.
42. The method of any one of clauses 36 to 41, wherein the trained neural network includes multiple subnetworks.
43. The method of clause 42, wherein a first subnetwork among the multiple subnetworks receives the inner retinal thickness map and outputs a first output, wherein a second subnetwork among the multiple subnetworks receives the reflectance intensity map and outputs a second output, and wherein a third subnetwork among the multiple subnetworks receives the first output, the second output, and the OCTA image, and outputs the first avascular map.
44. The method of clause 42 or 43 wherein at least one of the subnetworks includes a multi-scale block, the multi-scale block including: multiple first convolution blocks arranged in parallel, the first convolution blocks corresponding to different dilation rates; and a merge layer configured to combine the outputs from the first convolution blocks.
45. The method of any one of clauses 42 to 44, wherein at least one of the subnetworks includes multiple second convolution blocks arranged in series.
46. The method of clause 45, wherein at least one of the second convolution blocks includes at least one convolution layer.
47. The method of clause 46, wherein the at least one of the second convolution blocks further includes an upsampling layer and a concatenation layer.
48. The method of any one of clauses 42 to 47, wherein at least one of the second convolution blocks includes: multiple first convolution layers arranged in series; a second convolution layer arranged in parallel with the multiple first convolution layers; and a merge layer combining an output from the multiple first convolution layers and an output from the second convolution layer.
49. The method of any one of clauses 45 to 48, wherein at least one of the second convolution blocks includes: multiple first convolution layers arranged in series; and a merge layer combining an output from the multiple first convolution layers and an input to the multiple first convolution layers.
50. The method of any one of clauses 36 to 49, further including: generating an overlay image based on the OCTA image and the avascular map; and causing a clinical device to display the overlay image.
51. The method of any one of clauses 36 to 50, further including: quantifying an avascular area in a retina depicted in the first image based on the first avascular map.
52. The method of any one of clauses 36-51, wherein the trained neural network is trained using the method of clause 35.
53. A system, including: at least one processor; and memory storing instructions that, when executed by the at least one processor, cause the at least one processor to perform operations including: any one of the methods of clauses 1 to 52.
54. The system of clause 53, further including: an imaging device capturing at least one of the images.
55. A clinical device including the system of clause 53 or 54.
56. A computer-readable medium storing non-transitory instructions to perform operations including: any one of the methods of clauses 1 to 52.
57. A neural network according to any of clauses 1 to 52.
58. A system including an output device; at least one processor; and memory storing instructions that, when executed by the at least one processor, cause the system to perform operations including: generating a filtered reflectance image of an inner portion of a retina by applying a Gaussian filter to an optical coherence tomography (OCT) image of the inner portion; generating, using a first convolutional neural network (CNN), a first output image based on the filtered reflectance image; generating, using a second CNN, a second output image based on a thickness map image of the inner portion; generating a merged image by merging the first output image, the second output image, and an OCT angiography (OCTA) image of the retina, the OCTA image depicting at least a 3×3 $mm^2$ area of the retina and including at least one signal reduction area; generating, using a third CNN, an avascular map of the retina based on the merged image, the avascular map including a first group of pixels indicating at least one avascular region in the retina and a second group of pixels indicating at least one signal reduction area in the OCTA image; and causing the output device to display the avascular map overlying the OCTA image.
59. The system of clause 58, the merged image being a first merged image, wherein generating the avascular map includes generating a first input image based on the merged image; generating a third output image by cross-correlating, using at least one first convolutional layer in the third CNN, the first input image with a first filter using a first dilation rate; generating a second input image based on the merged image; generating a fourth output image by cross-correlating, using at least one second convolutional layer in the third CNN, the second input image with a second filter using a second dilation rate, the second dilation rate being different than the first dilation rate; and generating a second merged image by merging the third output image and the fourth output image.
60. The system of clause 58, wherein generating the avascular map further includes: generating a third input image based on the second merged image; generating, using a first encoder block in the third CNN, a fifth output image by cross-correlating at least one third filter with the third input image; generating, using a second encoder block in the third CNN, a sixth output image by cross-correlating at least one fourth filter with the fifth output image; and generating, using a decoder block in the third CNN, a seventh output image by: generating a concatenated image by concatenating the fifth output image and the sixth output image; and generating the seventh output image by cross-correlating at least one fifth filter with the concatenated image; and generating the avascular map based on the seventh output image.
61. The system of any one of clauses 58 to 60, the filtered reflectance image being a first filtered reflectance image, the retina being a first retina, the inner portion being a first inner portion, the thickness map image being a first thickness image, the OCTA image being a first OCTA image, wherein the operations further include:

training the first CNN, the second CNN, and the third CNN based on a training set that includes second filtered reflectance images of second retinas, second thickness maps images of the second retinas, second OCTA images of the second retinas, and second avascular maps of the second retinas, wherein the second retinas include at least one healthy retina and at least one retina with diabetic retinopathy (DR), and wherein the second OCTA images include signal reduction artifacts indicated by the second avascular maps.

62. The system of any one of clauses 58 to 61, wherein the at least one signal reduction area in the OCTA image includes at least one of a pupil vignetting area in the OCTA image, a floater shadow in the OCTA image, or a defocus area in the OCTA image.

63. The system of any one of clauses 58 to 62, wherein causing the output device to display the avascular map overlying the OCTA image includes: causing the output device to display the first group of pixels in a first color; and causing the output device to display the second group of pixels in a second color that is different than the first color.

64. The system of any one of clauses 58 to 63, wherein the avascular map indicates that the at least one avascular region is outside of the at least one signal reduction area.

CONCLUSION

The environments and individual elements described herein may of course include many other logical, programmatic, and physical components, of which those shown in the accompanying figures are merely examples that are related to the discussion herein.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect includes any effect that produces an inaccurate estimation of an avascular area and/or a signal reduction area (e.g., a difference of more than 20% of pixels between the estimated and manually segmented areas, such as an avascular area and/or a signal reduction area).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method, comprising:
    identifying a plurality of first images of a plurality of first retinas, the plurality of first images comprising thickness images of the first retinas, reflectance intensity maps of the first retinas, and Optical Coherence Tomography Angiography (OCTA) images of the first retinas;
    identifying a plurality of first avascular maps corresponding to the plurality of first images, wherein at least one of the first avascular maps a first level, a second level, and a third level, the first level indicating a vascular area in a particular one of the first images, the second level indicating an avascular area in the particular one of the first images, and the third level indicating a signal reduction area in the particular one of the first images; and
    training at least one convolutional neural network (CNN) based on the plurality of first images and the plurality of first avascular maps.

2. The method of claim 1, wherein the at least one CNN comprises multiple subnetworks, wherein a first subnetwork among the multiple subnetworks receives the inner retinal thickness maps and outputs a first output,
    wherein a second subnetwork among the multiple subnetworks receives the reflectance intensity maps and outputs a second output, and
    wherein a third subnetwork among the multiple subnetworks receives the first output, the second output, and the OCTA images, and outputs a plurality of second avascular maps.

3. The method of claim 2, wherein the multiple subnetworks comprise a plurality of convolution blocks,
    wherein training the at least one CNN comprises optimizing parameters associated with the convolution blocks to minimize a loss between the first avascular maps and the second avascular maps,
    wherein the loss is below a predetermined threshold.

4. The method of claim 2, wherein at least one of the subnetworks comprises a multi-scale block, the multi-scale block comprising:
    multiple first convolution blocks arranged in parallel, the first convolution blocks corresponding to different dilation rates; and
    a merge layer configured to combine the outputs from the first convolution blocks.

5. The method of claim 2, wherein at least one of the subnetworks comprises multiple second convolution blocks arranged in series,
    wherein at least one of the second convolution blocks comprises at least one convolution layer, and
    wherein the at least one of the second convolution blocks further comprises an upsampling layer and a concatenation layer.

6. The method of claim 2, wherein at least one of the subnetworks comprises multiple second convolution blocks arranged in series,
    wherein at least one of the second convolution blocks comprises:
    multiple first convolution layers arranged in series;
    a second convolution layer arranged in parallel with the multiple first convolution layers; and
    a merge layer combining an output from the multiple first convolution layers and an output from the second convolution layer.

7. A method comprising generating an avascular map by inputting an inner retinal thickness map of a retina, a reflectance intensity image of the retina, and an optical coherence tomography angiography (OCTA) image of the retina into at least one convolutional neural network (CNN).

8. The method of claim 7, further comprising generating the reflectance intensity image by applying a Multi-Gaussian filter on an OCT reflectance image of the retina.

9. The method of claim 7, wherein the avascular map indicates an avascular region of the OCTA image and a signal reduction area of the OCTA image.

10. The method of claim 9, wherein the avascular map further indicates a vascular region of the OCTA image.

11. The method of claim 7, wherein the neural network comprises multiple subnetworks, each of the subnetworks comprising:
a multi-scale block comprising multiple convolution blocks that apply different dilation rates and a merge block that concatenates outputs from the multiple convolution blocks.

12. A system, comprising:
at least one processor; and
memory storing instructions that, when executed by the at least one processor, cause the at least one processor to perform operations comprising:
inputting first images into a trained neural network, the first images comprising a thickness image of a first retina, a reflectance intensity map of the first retina, and an optical coherence tomography angiography (OCTA) image of the first retina; and
receiving a first avascular map from the trained neural network, the first avascular map corresponding to the first images, wherein the first avascular map comprises first, second, and third regions, the first region indicating a vascular of the OCTA image, the second region indicating an avascular area of the OCTA image, and the third region indicating a signal reduction area of the OCTA image.

13. The system of claim 12, wherein the trained neural network comprises multiple subnetworks.

14. The system of claim 13, wherein a first subnetwork among the multiple subnetworks receives the inner retinal thickness map and outputs a first output,
wherein a second subnetwork among the multiple subnetworks receives the reflectance intensity map and outputs a second output, and
wherein a third subnetwork among the multiple subnetworks receives the first output, the second output, and the OCTA image, and outputs the first avascular map.

15. The system of claim 13 wherein at least one of the subnetworks comprises a multi-scale block, the multi-scale block comprising:
multiple first convolution blocks arranged in parallel, the first convolution blocks corresponding to different dilation rates; and
a merge layer configured to combine the outputs from the first convolution blocks.

16. The system of claim 13, wherein at least one of the subnetworks comprises multiple second convolution blocks arranged in series,
wherein at least one of the second convolution blocks comprises at least one convolution layer, and
wherein the at least one of the second convolution blocks further comprises an upsampling layer and a concatenation layer.

17. The system of claim 13, wherein at least one of the second convolution blocks comprises:
multiple first convolution layers arranged in series;
a second convolution layer arranged in parallel with the multiple first convolution layers; and
a merge layer combining an output from the multiple first convolution layers and an output from the second convolution layer.

18. The system of claim 13, wherein at least one of the second convolution blocks comprises:
multiple first convolution layers arranged in series; and
a merge layer combining an output from the multiple first convolution layers and an input to the multiple first convolution layers.

19. The system of claim 12, wherein the operations further comprise:
generating an overlay image based on the second and third regions of the avascular map and the OCTA image; and
causing a clinical device to display the overlay image.

20. The method of claim 12, wherein the operations further comprise:
quantifying an avascular area in a retina depicted in the first image based on the first avascular map.

* * * * *